US008706216B2

(12) United States Patent
Efimov et al.

(10) Patent No.: US 8,706,216 B2
(45) Date of Patent: *Apr. 22, 2014

(54) METHOD AND DEVICE FOR THREE-STAGE ATRIAL CARDIOVERSION THERAPY

(75) Inventors: Igor Efimov, Wildwood, MO (US); Wenwen Li, St. Louis, MO (US); Ajit Janardhan, St. Louis, MO (US)

(73) Assignee: The Washington University, St. Louis, MO (US)

( * ) Notice: Subject to any disclaimer, the term of this patent is extended or adjusted under 35 U.S.C. 154(b) by 52 days.

This patent is subject to a terminal disclaimer.

(21) Appl. No.: 13/349,517

(22) Filed: Jan. 12, 2012

(65) Prior Publication Data
US 2012/0209343 A1 Aug. 16, 2012

Related U.S. Application Data

(63) Continuation-in-part of application No. 12/776,196, filed on May 7, 2010, now Pat. No. 8,560,066, which is a continuation-in-part of application No. 12/333,256, filed on Dec. 11, 2008.

(60) Provisional application No. 61/012,861, filed on Dec. 11, 2007.

(51) Int. Cl.
*A61N 1/368* (2006.01)
*A61N 1/39* (2006.01)
*A61N 1/362* (2006.01)

(52) U.S. Cl.
CPC ............. *A61N 1/3956* (2013.01); *A61N 1/3624* (2013.01); *A61N 1/395* (2013.01)
USPC ........................................... 607/5

(58) Field of Classification Search
USPC ....................... 607/4–5, 10, 14, 28
See application file for complete search history.

(56) References Cited

U.S. PATENT DOCUMENTS 3,729,008 A 4/1973 Berkovits
3,738,370 A 6/1973 Charms
(Continued)

FOREIGN PATENT DOCUMENTS

EP 0 393 265 A1 10/1990
EP 1 062 971 A1 12/2000
(Continued)

OTHER PUBLICATIONS

Application and File History for U.S. Appl. No. 12/333,257, filed Dec. 11, 2008, inventors Efimov et al.
(Continued)

*Primary Examiner* — Carl H Layno
*Assistant Examiner* — Jon Eric C Morales
(74) *Attorney, Agent, or Firm* — Patterson Thuente Pedersen, P.A.

(57) ABSTRACT

Methods and apparatus for a three-stage atrial cardioversion therapy that treats atrial arrhythmias within pain tolerance thresholds of a patient. An implantable therapy generator adapted to generate and selectively deliver a three-stage atrial cardioversion therapy and at least two leads, each having at least one electrode adapted to be positioned proximate the atrium of the patient. The device is programmed for delivering a three-stage atrial cardioversion therapy via both a far-field configuration and a near-field configuration of the electrodes upon detection of an atrial arrhythmia. The three-stage atrial cardioversion therapy includes a first stage for unpinning of one or more singularities associated with an atrial arrhythmia, a second stage for anti-repinning of the one or more singularities, both of which are delivered via the far-field configuration of the electrodes, and a third stage for extinguishing of the one or more singularities delivered via the near-field configuration of the electrodes.

27 Claims, 29 Drawing Sheets

(56) References Cited

U.S. PATENT DOCUMENTS

| | | | |
|---|---|---|---|
| 3,942,536 A | 3/1976 | Mirowski et al. |
| 4,136,703 A | 1/1979 | Wittkampf |
| 4,384,585 A | 5/1983 | Ziped |
| 4,727,877 A | 3/1988 | Kallok |
| 5,107,834 A | 4/1992 | Ideker et al. |
| 5,199,429 A | 4/1993 | Kroll et al. |
| 5,265,600 A | 11/1993 | Adams et al. |
| 5,275,621 A | 1/1994 | Mehra |
| 5,282,836 A | 2/1994 | Kreyenhagen et al. |
| 5,306,291 A | 4/1994 | Kroll et al. |
| 5,330,509 A | 7/1994 | Kroll et al. |
| 5,334,219 A | 8/1994 | Kroll |
| 5,365,391 A | 11/1994 | Sugiyama et al. |
| 5,372,605 A | 12/1994 | Adams et al. |
| 5,383,907 A | 1/1995 | Kroll |
| 5,387,613 A | 2/1995 | Goldberg et al. |
| 5,391,186 A | 2/1995 | Kroll |
| 5,403,356 A | 4/1995 | Hill et al. |
| 5,405,363 A | 4/1995 | Kroll |
| 5,407,444 A | 4/1995 | Kroll |
| 5,413,591 A | 5/1995 | Knoll |
| 5,433,729 A | 7/1995 | Adams et al. |
| 5,489,293 A | 2/1996 | Pless et al. |
| 5,545,182 A | 8/1996 | Stotts et al. |
| 5,545,204 A | 8/1996 | Cammilli et al. |
| 5,562,708 A | 10/1996 | Combs et al. |
| 5,620,464 A | 4/1997 | Kroll et al. |
| 5,620,468 A | 4/1997 | Mongeon et al. |
| 5,674,248 A | 10/1997 | Kroll et al. |
| 5,676,687 A | 10/1997 | Ayers |
| 5,683,429 A | 11/1997 | Mehra |
| 5,766,226 A | 6/1998 | Pedersen |
| 5,792,187 A | 8/1998 | Adams |
| 5,797,967 A | 8/1998 | KenKnight |
| 5,813,999 A | 9/1998 | Ayers et al. |
| 5,840,079 A | 11/1998 | Warman et al. |
| 5,925,066 A | 7/1999 | Kroll et al. |
| 5,928,270 A | 7/1999 | Ramsey, III |
| 5,995,871 A | 11/1999 | Knisley |
| 6,070,081 A | 5/2000 | Takahashi et al. |
| 6,081,746 A | 6/2000 | Pendekanti et al. |
| 6,085,116 A | 7/2000 | Pendekanti et al. |
| 6,085,119 A | 7/2000 | Scheiner et al. |
| 6,091,991 A | 7/2000 | Warren |
| 6,094,596 A | 7/2000 | Morgan |
| 6,141,588 A | 10/2000 | Cox et al. |
| 6,157,859 A | 12/2000 | Alt |
| 6,178,351 B1 | 1/2001 | Mower |
| 6,185,459 B1 | 2/2001 | Mehra et al. |
| 6,205,357 B1 | 3/2001 | Ideker et al. |
| 6,233,483 B1 | 5/2001 | Causey, III et al. |
| 6,246,906 B1 | 6/2001 | Hsu et al. |
| 6,292,691 B1 | 9/2001 | Pendekanti et al. |
| 6,327,500 B1 | 12/2001 | Cooper et al. |
| 6,463,330 B1 | 10/2002 | Rabinovitch |
| 6,510,342 B1 | 1/2003 | Park et al. |
| 6,526,317 B2 | 2/2003 | Hsu et al. |
| 6,556,862 B2 | 4/2003 | Hsu et al. |
| 6,567,698 B2 | 5/2003 | Herleikson |
| 6,587,720 B2 | 7/2003 | Hsu et al. |
| 6,711,442 B1 | 3/2004 | Swerdlow et al. |
| 6,745,081 B1 | 6/2004 | Helland et al. |
| 6,754,525 B1 | 6/2004 | Province et al. |
| 6,763,266 B1 | 7/2004 | Kroll |
| 6,813,516 B2 | 11/2004 | Ujhelyi et al. |
| 6,847,842 B1 | 1/2005 | Rodenhiser et al. |
| 6,937,896 B1 | 8/2005 | Kroll |
| 7,006,867 B1 | 2/2006 | Kroll |
| 7,020,517 B2 | 3/2006 | Weiner |
| 7,047,071 B2 | 5/2006 | Wagner et al. |
| 7,079,891 B1 | 7/2006 | Kroll |
| 7,110,811 B2 | 9/2006 | Wagner et al. |
| 7,113,822 B1 | 9/2006 | Kroll |
| 7,120,490 B2 | 10/2006 | Chen et al. |
| 7,127,292 B2 | 10/2006 | Warman et al. |
| 7,139,611 B1 | 11/2006 | Kroll et al. |
| 7,142,927 B2 | 11/2006 | Benser et al. |
| 7,142,928 B2 | 11/2006 | Sharma et al. |
| 7,155,286 B1 | 12/2006 | Kroll et al. |
| 7,181,276 B1 | 2/2007 | Province et al. |
| 7,480,351 B2 | 1/2009 | Hiatt, Jr. et al. |
| 7,532,933 B2 | 5/2009 | Hastings et al. |
| 7,647,109 B2 | 1/2010 | Hastings et al. |
| 7,848,823 B2 | 12/2010 | Drasler et al. |
| 7,899,537 B1 | 3/2011 | Kroll et al. |
| 7,925,343 B1 | 4/2011 | Min et al. |
| 8,032,218 B2 | 10/2011 | Wong et al. |
| 8,175,702 B2 | 5/2012 | Efimov et al. |
| 8,204,605 B2 | 6/2012 | Hastings et al. |
| 2002/0128565 A1 | 9/2002 | Rudy |
| 2003/0083727 A1 | 5/2003 | Casavant et al. |
| 2003/0130703 A1 | 7/2003 | Florio et al. |
| 2003/0220676 A1 | 11/2003 | Helland |
| 2004/0111123 A1 | 6/2004 | Ware et al. |
| 2005/0096701 A1 | 5/2005 | Donovan et al. |
| 2005/0154420 A1 | 7/2005 | Diaz et al. |
| 2006/0161206 A1 | 7/2006 | Efimov et al. |
| 2007/0021793 A1 | 1/2007 | Voegele et al. |
| 2007/0088395 A1 | 4/2007 | Province et al. |
| 2009/0062877 A1 | 3/2009 | Krinski et al. |
| 2009/0204164 A1 | 8/2009 | Efimov et al. |
| 2011/0009916 A1* | 1/2011 | Efimov et al. ............ 607/5 |
| 2011/0029032 A1 | 2/2011 | Bardy et al. |
| 2012/0203297 A1 | 8/2012 | Efimov et al. |

FOREIGN PATENT DOCUMENTS

| | | |
|---|---|---|
| GB | 2 025 236 A | 1/1980 |
| WO | WO 96/11035 | 4/1996 |
| WO | WO 2006/042295 A1 | 4/2006 |
| WO | WO 2008/063498 A1 | 5/2008 |

OTHER PUBLICATIONS

Application and File History for U.S. Appl. No. 12/776,196, filed May 7, 2010, inventors Efimov et al.

Application and File History for U.S. Appl. No. 13/349,527, filed Jan. 12, 2012, inventors Efimov et al.

Translation and Notice of Reason for Rejection mailed Aug. 7, 2012 for Japanese Application No. 2010-538168.

Supplementary Partial European Search Report for European Application No. 08858734.0 dated Nov. 17, 2011. 5 pages.

Anderson, "The Anatomy of the Atrioventricular Node". Heart Rhythm Society. 7 pages. Apr. 16, 2012.

Davidenko et al., "Stationary and drifting spiral waves of excitation in isolated cardiac muscle," Nature, vol. 355, pp. 349-351, Jan. 23, 1992.

Gray et al., "Spatial and temporal organization during cardiac fibrillation," Nature, vol. 392, pp. 75-78, May 14, 1998.

Witkowski et al, "Spatiotemporal evolution of ventricular fibrillation," Nature, vol. 392, pp. 78-82, Mar. 5, 1998.

Cherry et al, "Visualization of spiral and scroll waves in simulated and experimental cardiac tissue", New J. Phys., vol. 10, pp. 125016-125059, 2008.

Koster et al., "A randomized trial comparing monophasic and biphasic waveform shocks for external cardioversion of atrial fibrillation," Am. Heart. J. vol. 147, pp. e1-e7, 2004.

Babbs et al., "Therapeutic indices for transchest defibrillator shocks: Effective, damaging, and lethal electrical doses," Am. Heart J., vol. 99, No. 6, pp. 734-738, Jun. 1980.

Santini et al., "Single Shock Endocavitary Low Energy Intracardiac Cardioversion of Chronic Atrial Fibrillation," J. Interv. Card. Electrophysiol., vol. 3, pp, 45-51, 1999.

Sakurai et al., "Design and Control of Wave Propagation Patterns in Excitable Media," Science, vol. 296, pp. 2009-2012, Jun. 14, 2002.

Rappel et al, "Spatiotemporal Control of Wave Instabilities in Cardiac Tissue," Phys. Rev. Lett., vol. 83, No. 2, pp. 456-459, Jul. 12, 1999.

Fenton et al., "Multiple mechanisms of spiral wave breakup in a model of cardiac electrical activity," Chaos, vol. 12, No, 3, pp. 852-892, Sep. 2002.

(56) References Cited

OTHER PUBLICATIONS

Fenton et al., "Vortex dynamics in three-dimensional continuous myocardium with fiber rotation: Filament instability and fibrillation," Chaos, vol. 8, No. 1, pp. 20-47, Mar. 1998.
Mackenzie, "Making sense of a heart gone wild," Science, vol. 303, pp. 786-787, Feb. 6, 2004.
Walcott et al., "Do clinically relevant transthoracic defibrillation energies cause myocardial damage and dysfunction?" Resuscitation, vol. 59, pp. 59-70, 2003.
Fenton et al., "Termination of Atrial Fibrillation Using Pulsed Low-Energy Far-Field Stimulation," Circulation, vol. 120, pp. 467-476, 2009.
Plonsey, "The Nature of Sources of Bioelectric and Biomagnetic Fields," Biophys. J., vol. 39, pp. 309-312, 1982.
Fast et al., "Activation of Cardiac Tissue by Extracellular Electrical Shocks: Formation of 'Secondary Sources' at Intercellular Clefts in Monolayers of Cultured Myocytes," Circ. Res., vol. 82, pp. 375-385, 1998.
Sambelashvili et al., "Virtual electrode theory explains pacing threshold increase caused by cardiac tissue damage," Am. J. Physiol. Heart Circ. Physiol., vol. 286, pp. H2183-H2194, 2004.
Hooks et al, "Cardiac Microstructure: Implications for Electrical Propagation and Defibrillation in the Heart," Circ. Res., vol. 91, pp. 331-338, 2002.
Trayanova et al., "Modeling Defibrillation: Effects of Fiber Curvature," J. Electrocardiol., vol. 31 (suppl.), pp. 23-29, 1998.
Roth et al., "A Bidomain Model for the Extracellular Potential and Magnetic Field of Cardiac Tissue," IEEE Trans. Biomed. Eng., vol. 33, No. 4, pp. 467-469, Apr. 1986.
Murray, "The Physiological Principle of Minimum Work: I. The Vascular System and the Cost of Blood Volume," Proc. Natl. Acad. Sci. USA, vol. 12, pp. 207-214, 1926.
Kassab, "Scaling laws of vascular trees: of form and function," Am. J. Physiol. Heart Circ. Physiol., vol. 290, pp. H894-H903, 2006.
Maleckar et al., "Polarity reversal lowers activation time during diastolic field stimulation of the rabbit ventricles: insights into mechanisms," Am. J. Physiol. Heart Circ, Physiol., vol. 295, pp. H1626-1633, 2008.
Kirchhof et al, "Regional entrainment of Atrial Fibrillation Studied by High-Resolution Mapping in Open-Chest Dogs," Circulation, vol. 88, pp. 736-749, 1993.
Pumir et al, "Wave Emission from Heterogeneities Opens a Way to Controlling Chaos in the Heart," Phys. Rev. Lett., vol. 99, pp. 208101-1, 2007.
Gray et al, "Termination of spiral waves during cardiac fibrillation via shock-induced phase resetting," Proc. Natl. Acad. Sci. USA, vol. 102, No. 13, pp. 4672-4677, Mar. 29, 2005.
International Search Report for International Application No. PCT/US2007/023836 dated Apr. 9, 2008, 7 pages.
Gray et al., "Several small shocks beat one big one", vol. 475. Jul. 14, 2011. pp. 181-182.
Ladwig et al., "Absence of an Impact of Emotional Distress on the Perception of Intracardiac Shock Discharges," International Journal of Behavioral Medicine, 2003, 10(1):56-65, USA.
Fishler et al., "Spatiotemporal Effects of Syncytial Heterogeneities on Cardiac Far-field Excitations during Monophasic and Biphasic Shocks", Journal of Cardiovascular Electrophysiolgy, 1998, 9(12):1310-24, USA.
Efimov et al., "Virtual Electrode-Induced Phase Singularity: A Basic Mechanism of Defibrillation Failure," Circulation Research, 1998, 82(8):918-25, USA.
Efimov et al., "Transmembrane Voltage Changes Produced by Real and Virtual Electrodes During Monophasic Defibrillation Shock Delivered by an Implantable Electrode," Journal of Cardiovascular Electrophysiolgy, 1997, 8(9):1031-45, USA.
Cheng et al., "Virtual Electrode-Induced Reexcitation: A Mechanism of Defibrillation," Circulation Research, 1999, 85(11):1056-66, USA.

Fishler, "Syncytial Heterogeneity as a Mechanism Underlying Cardiac Far-Field Stimulation During Defibrillation-Level Shocks," Journal of Cardiovascular Electrophysiolgy, 1998, 9(4):384-94, USA.
Tsukerman et al., "Defibrillation of the Heart by a Rotating Current Field," Kardiologiia, 1973, 13(12):75-80, USA.
Zheng et al., "Reduction of the Internal Atrial Defibrillation Threshold with Balanced Orthogonal Sequential Shocks," Journal of Cardiovascular Electrophysiolgy, 2002; 13(9):904-9, USA.
Hucker et al., "Atrioventricular conduction with and without AV nodal delay: two pathways to the bundle of His in the rabbit heart", Am J. Physiol. Heart Circ. Physiol., 2007, 293:H1122-H1130, USA.
Mowrey et al., "Membrane Time Constant During Internal Defibrillation Strength Shocks in Intact Heart: Effects of $Na^+$ and $Ca^{2+}$ Channel Blockers," J. Cardiovascular Electrophysiology, Apr. 25, 2004, Jun. 8, 2008, and Jan. 2009, 20(1):85-92, USA.
European Patent Office, European Office Action for European Application No. 05825356.8, dated Oct. 5, 2009, 6 pages, Munich, Germany.
Written Opinion of the International Searching Authority for International Application No. PCT/US2008/086483, dated Jun. 25, 2009, 6 pages.
Sepulveda et al., "Current injection into a two-dimensional anisotropic bidomain", Biophys. J., vol. 55, May 1989, pp. 987-999, USA.
Allessie et al., "Regional Control of Atrial Fibrillation by Rapid Pacing in Conscious Dogs", Circulation, vol. 84, No. 4, Oct. 1991, pp. 1689-1697, USA.
Daoud et al., "Response of Type I Atrial Fibrillation to Atrial Pacing in Humans", Circulation, vol. 94, No. 5, 1996, 13 pages, USA.
Disertori et al., "Antitachycardia pacing therapies to terminate atrial tachyarrhythmias: the AT500 Italian Registry", European Heart Journal Supplements, 2001, pp. 16-24, USA.
Pumir et al., "Unpinning of a Rotating Wave in Cardiac Muscle by an Electric Field", J. Theor, Biol., vol. 199, 1999, pp. 311-319, USA.
Grosu et al., "Learning and Detecting Emergent Behavior in Networks of Cardiac Myocytes", *Communications of the ACM*, Mar. 2009, pp. 97-104, vol. 52, No. 3.
Ripplinger et al., "Mechanisms of unpinning and termination of ventricular tachycardia", *Am J. Physiol. Heart Circ. Physiol.*, 2006, pp. H184-H192.
International Search Report for International Application No. PCT/US2005/040187 dated Feb. 24, 2009.
N. S. Peters et al., "Disturbed Connexin43 Gap Junction Distribution Correlates With the Location of Reentrant Circuits in the Epicardial Border Zone of Healing Canine Infarcts That Cause Ventricular Tachycardia," *Circulation*, 1997, 95:988-996.
J. T. Niemann et al., "Intracardiac Voltage Gradients during Transthoracic Defibrillation: Implications for Postshock Myocardial Injury," *Acad. Emerg. Med.*, Feb. 2005, 12(2):99-105.
I. Kodama et al., "Aftereffects of high-intensity DC stimulation of the electromechanical performance of ventricular muscle", *Am J. Physiol.*, 1994, 267:H248-H258.
H. G. Li et al., "Defibrillation Shocks Produce Different Effects on Purkinje Fibers and Ventricular Muscle: Implications for Successful Defibrillation, Refibrillation and Postshock Arrhythmia", *J Am Coll Cardiol*, 1993, 22:607-614.
X. Zhou et al., "Epicardial Mapping of Ventricular Defibrillation With Monophasic and Biphasic Shocks in Dogs," *Circulation Research*, Jan. 1993, 72(1):145-160.
L. Li et al., "Mechanisms of enhanced shock-induced arrhythmogenesis in the rabbit heart with healed myocardial infarction," *Am. J. Physiol. Heart Circ Physiol.*, May 3, 2005, 289:H1054-H1068.
A. Sambelashvili et al., "Nonlinear effects in subthreshold virtual electrode polarization," *Am. J. Physiol. Heart Circ, Physiol.*, 2003, 284(6):H2368-H2374.
F. Aguel et al., "Advances in Modeling Cardiac Defibrillation," *Int'l Journal of Bifurcation & Chaos*, 13(12):3791-3803.
M. Hillebrenner et al., "Postshock arrhythmogenesis in a slice of the canine heart," *J. Cardiovasc. Electrophys.*, 2003, 14:S249-S256.

(56) References Cited

OTHER PUBLICATIONS

N. Trayanova et al., "Virtual Electrode-Induced Positive and Negative Graded Responses: New Insights into Fibrillation Induction and Defibrillation," *J. Cardiovascular Electrophysicology*, 2003, 14(7):756-763.

C. Larson et al., "Analysis of Electrically-Induced Reentrant Circuits in a Sheet of Myocardium," *Annals Biomed. Eng.*, 2003, 31:768-780.

I. R. Efimov, "Filbrillatin or Neurillation: Back to the future in our concepts of sudden cardiac death?", *Circ. Res.*, May 30, 2003, 92(10):1062-1064.

I. R. Efimov et al., "Diastolic Shocking Experience: Do Virtual Anodes Exist Only During Systole?", *J. Cardiovascular Electrophysiology*, Nov. 2003, 14(11):1223-1224.

I. R. Efimov et al,, Fast Fluorescent Mapping of Electrical Activity in the Heart: Practical Guide to Experimental Design and Applications, Chapter 7, pp. 131-156.

Y. Cheng et al., "Shock-induced arrhythmogenesis is enhanced by 2,3-butanedione monoxime compared with cytochalasin D," *Am. J. Physiol. Heart. Circ. Physiol.*, 2004, 286:H310-H318.

S. Takagi et al., "Unpinning and Removal of a Rotating Wave in Cardiac Muscle", *Phys. Review Letters*, Jul. 30, 2004, 93(5):058101-1-058101-4.

L. Li et al., "Effects of Lidocaine on Shock-Induced Vulnerability", *J. Cardiovascular Electrophysiology*, Oct. 2003, 14(10):S237-S248.

Y. Cheng et al., "Mechanisms of Shock-Induced Arrhythmogenesis During Acute Global Ischemia", *Am J Physiol. Heart Circ. Physiol.*, Jun. 2002, 282(6):H2141-51.

F. Qu et al., "Mechanisms of Superiority of Ascending Ramp Waveforms: New Insights into Mechanisms of Shock-induced Vulnerability and Defibrillation," *Am, J. Physiol, Heart Circ. Physiol.*, 2005, 289:H569-H577.

T. Ashihara et al., "Spiral Wave Control by a Localized Stimulus: A Bidomain Model Study," *J. Cardiovascular Electrophysiology*, Feb. 2004 15(2):226-233.

C. Ramanathan, "Noninvasive electrocardiographic imaging for cardiac electrophysiology and arrhythmia," *Nature Medicine*, Apr. 2004, 10(4):422-428.

V. Nikolski et al., "Fluorescent Imaging of a Dual-Pathway Atrioventricular-Nodal Conduction System," *Circ Res.*, Feb. 16, 2001, pp. 1-7.

F. Qu et al., "The Gurvich waveform has lower defibrillation threshold than the Zoll waveform and the truncated exponential waveform in the rabbit heart," *Can. J. Physiol. Pharmacol.*, 2005, 83:152-160.

PCT International Search Report for International Application No. PCT/US2011/033547 dated Jan. 17, 2012, 4 pages.

PCT Written Opinion dated International Application No. PCT/US2011/033547 Jan. 17, 2012, 4 pages.

Cartee et al., "The Transient Subthreshold Response of Spherical and Cylindrical Cell Models to Extracellular Stimulation", IEEE Trans. Biomed. Eng., vol. 39, No. 1, Jan. 1992, pp. 76-85.

Ideker et al., "Correlation Among Fibrillation, Defibrillation and Cardiac Pacing", Pacing Clin. Electrophysiol., vol. 18, Mar. 1995, pp. 512-525.

Sobie et al., "A Generalized Activating Function for Predicting Virtual Electrodes in Cardiac Tissue", Biophys. J., vol. 73, Sep. 1997, pp. 1410-1423.

Trayanova et al., "The Response of a Spherical Heart to a Uniform Electric Field: A Bidomain Analysis of Cardiac Stimulation", J, IEEE trans. Biomed. Eng., vol. 40, No. 9, Sep. 1993, pp. 899-908.

Japanese Notice of Reasons for Rejection for Japanese Application No. 2010538168 dated Mar. 26, 2013.

Australian Patent Examination Report No. 1 for Australian Application No. 2008335087 dated Feb. 21, 2013.

Chinese Office Action from Chinese Application No. 200880126712.0 dated May 2, 2013.

Chinese Office Action from Chinese Application No. 200880126712,0 dated Nov. 27, 2012.

Chebbok et al., Low Energy Anti-Fibrillation Pacing (LEAP): A Gental, non traumatic defibrillation Option. European Heart Journal 33: 381-381 Suppl. 1 Aug. 2012.

International Preliminary Report on Patentability for International Application No. PCT/US2011/033547 dated Nov. 22, 2012.

Australian Patent Examination Report No. 1 for Australian Application No. 2011248794 dated Aug. 30, 2013.

European Search Report for European Application No. 11777847 mailed Nov. 5, 2013.

\* cited by examiner

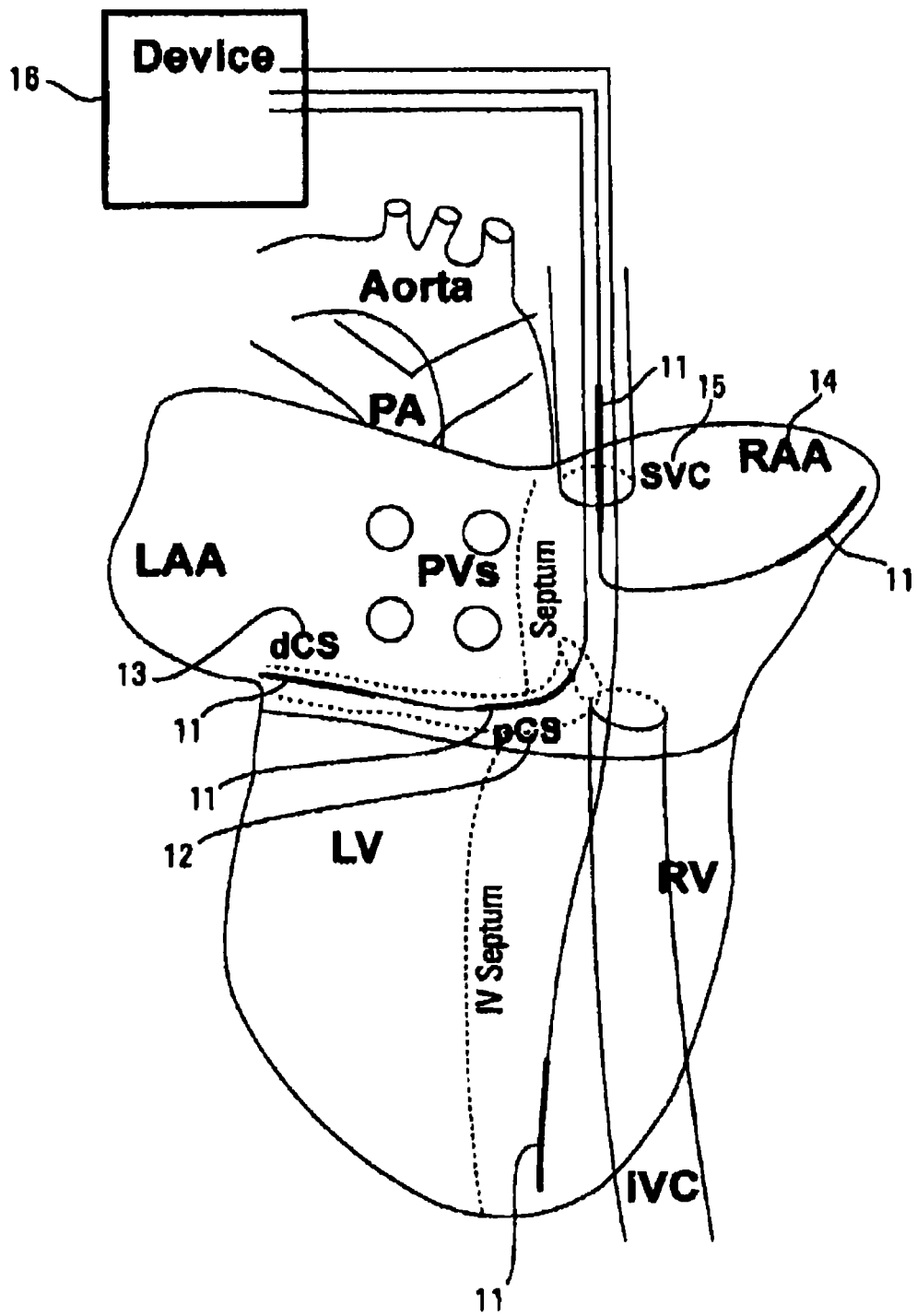

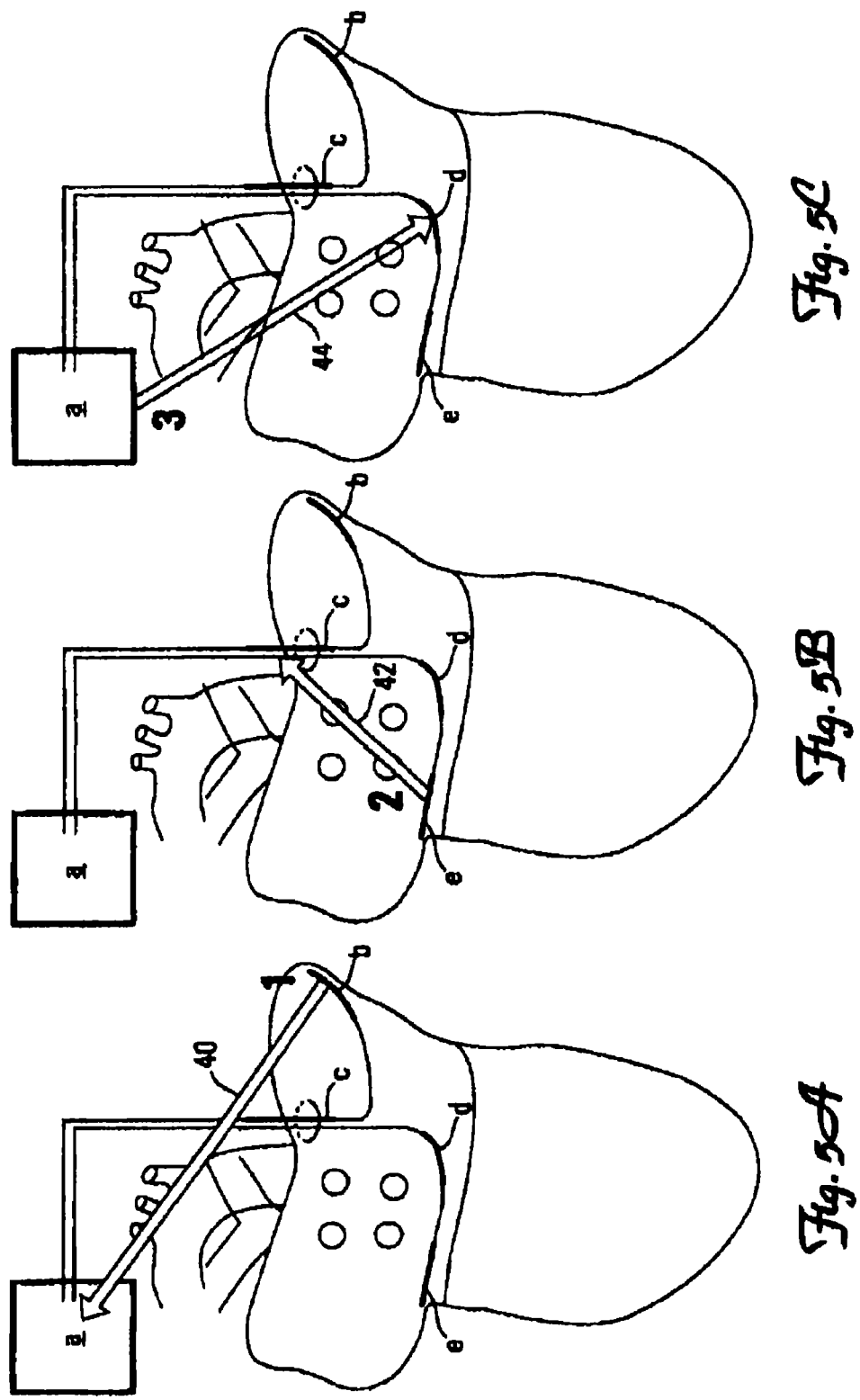

Summary of shocks amplitude for canine right atria experiments (n=6)

| Shocks | Voltage (V/cm) | Energy (Joules) |
|---|---|---|
| Field Excitation Threshold | 0.14 ± 0.12 | 0.005 ± 0.0001 |
| At Minimum Termination | 0.2 ± 0.06 | 0.018 ± 0.001 |
| AF Minimum Termination 1 pulse | 7.44 ± 3.27 | 2.6 ± 0.78 |
| 2 pulses | 3.11 ± 0.74 | 0.44 ± 0.04 |
| 3 pulses | 3.37 ± 0.73 | 0.48 ± 0.03 |

Other parameters of experiments
- Acetylcholine Concentration   4.55 ± 2.95 μM
- Terminated AF Cycle Length   53.32 ± 3.98 ms
- % AF Cycle Length Terminated
  - 2 pulses   101.25 ± 26.39
  - 3 pulses   99.48 ± 19.06

Fig. 8

| Default electric field therapy sequence based on reentry circuit location | | | |
|---|---|---|---|
| Zone (see Figure 7) | First applied electric field (see Figures 5A-C) | Second applied electric field (see Figures 5A-C) | Third applied electric field (see Figures 5A-C) |
| Zone 310 | Electrode (b) to electrode (a) | Electrode (e) to electrode (c) | Electrode (a) to electrode (d) |
| Zone 320 | Electrode (a) to electrode (d) | Electrode (b) to electrode (a) | Electrode (e) to electrode (c) |
| Zone 330 | Electrode (b) to electrode (a) | Electrode (e) to electrode (c) | Electrode (a) to electrode (d) |
| Zone 340 | Electrode (e) to electrode (c) | Electrode (a) to electrode (d) | Electrode (b) to electrode (a) |
| Zone 350 | Electrode (a) to electrode (d) | Electrode (b) to electrode (a) | Electrode (e) to electrode (c) |

Fig. 9

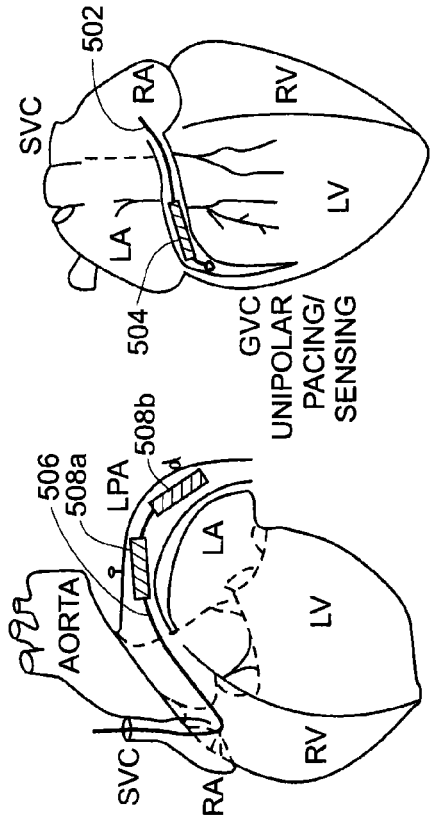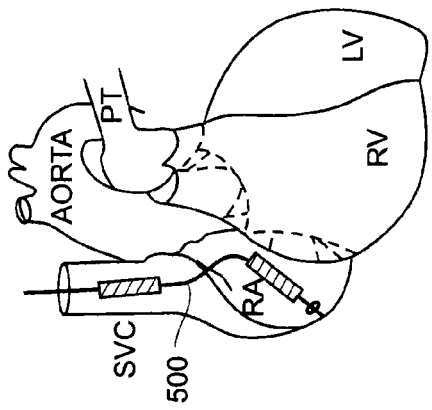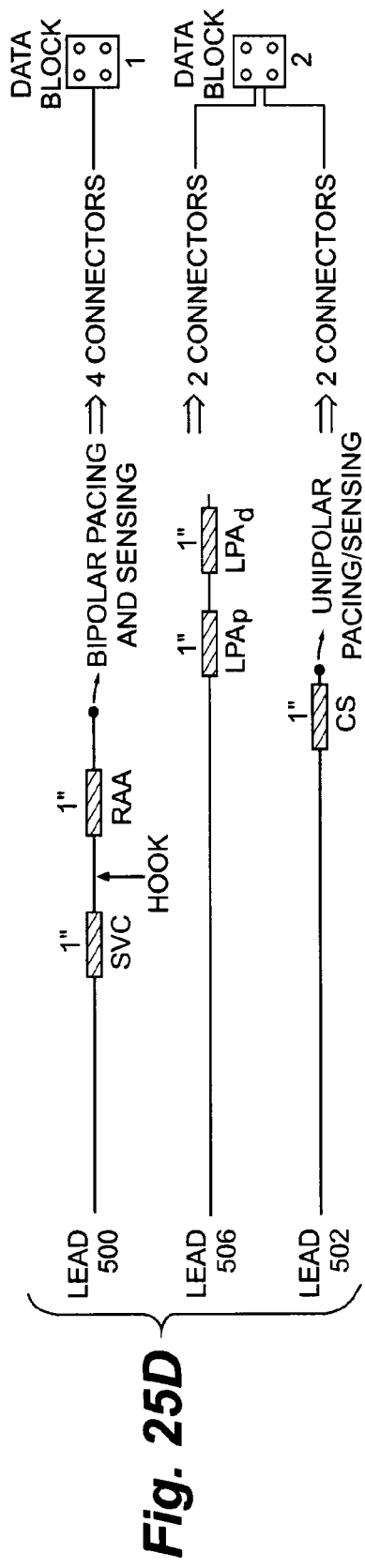

METHOD AND DEVICE FOR THREE-STAGE ATRIAL CARDIOVERSION THERAPY

RELATED APPLICATIONS

The present application is a continuation-in-part of U.S. patent application Ser. No. 12/776,196, filed May 7, 2010, is now U.S. Pat. No. 8,560,066 which is a continuation-in-part of U.S. patent application Ser. No. 12/333,256, filed Dec. 11, 2008, which claims the benefit of U.S. Provisional Application No. 61/012,861, filed Dec. 11, 2007, each of which is incorporated herein by reference.

FIELD OF THE INVENTION

The present disclosure relates generally to the treatment of atrial arrhythmias, such as atrial fibrillation ("AF") and atrial flutter ("AFl"). More particularly, the present disclosure relates to devices and methods of using low-energy electrical stimuli from an implantable device that delivers a three-stage atrial cardioversion therapy to destabilize and extinguish reentry mechanisms that maintain AF and AFl.

BACKGROUND OF THE INVENTION

Atrial tachyarrhythmias are the most common atrial arrhythmia, presently estimated to affect approximately 2.3 million Americans. There are two primary forms of atrial tachyarrhythmias, AF and AFl, with relative occurrence in their chronic forms of about 10:1, respectively. Current projections suggest that by the year 2050, between about twelve and about fifteen million Americans will suffer from AF. The enormity of the problem is magnified by its well-described clinical consequences: thromboembolic stroke, congestive heart failure ("CHF"), cognitive dysfunction, and possibly increased mortality.

Many different factors can promote the initiation and maintenance of AF and AFl. Several cardiac disorders can predispose patients to AF, including coronary artery disease, pericarditis, mitral valve disease, congenital heart disease, CHF, thyrotoxic heart disease, and hypertension. Many of these are thought to promote AF by increasing atrial pressure and/or causing atrial dilation. AF also occurs in individuals without any evidence of heart or systemic disease, a condition known as "lone AF," which primarily involves the autonomic nervous system.

Both AF and AFl are maintained by a reentry mechanism. Specifically, atrial tissue continually excites itself, creating reentrant, i.e. circular or tornado-like patterns of excitation. AFl is generally defined as a macro-reentrant circuit, which can rotate around a functional or anatomic line of block. Major anatomical structures are usually involved in defining one or several simultaneous reentry circuit(s), including the region between superior and inferior venae cavae in the right atrium, and the pulmonary vein region in the left atrium. If the cycle length ("CL") of the reentry remains relatively long, one-to-one conduction can remain throughout the entire atria and AFl can be observed. However, if the CLs of reentry circuits are sufficiently short, waves of excitation produced by the reentrant circuit break up in the surrounding atrial tissue and AF can ensue. The morphology of electrograms during AFl or AF depends on the anatomic location and frequency of reentry circuits that cause the arrhythmia.

There are clear interactions between AF and AFl. AFl is defined as the presence of a single, constant, and stable reentrant circuit. AF, on the other hand, can be due to random activation in which multiple reentrant wavelets of the leading circle type (mother rotor) continuously circulate in directions determined by local excitability, refractoriness, and anatomical structure. AF can be converted to AFl, and vice versa, spontaneously or as a result of an intervention, such as drug administration, DC cardioversion, or atrial pacing.

AF is the most prevalent clinical arrhythmia in the world and, with an aging population, has the potential of becoming an increasing cause of morbidity and mortality. Although several options for pharmaceutical treatment exist, for some patients, particularly those with paroxysmal AF, drug therapy can be ineffective. In addition, anti-arrhythmic drugs can have serious pro-arrhythmic side effects. Therefore, non-pharmacologic treatments of AF are needed.

One alternative to pharmacological treatment of AF is a cardiac ablation procedure. While there have been many advances in ablative techniques, these procedures are not without risks. Such risks can include cardiac perforation, esophageal injury, embolism, phrenic nerve injury, and pulmonary vein stenosis. There are also implantable devices currently on the market for the treatment of atrial tachyarrhythmias. Some of these devices apply near-field overdrive pacing, also known as antitachycardia pacing ("ATP"); conventional high-energy far field defibrillation shocks; or a combination thereof. As described, for example in U.S. Pat. No. 5,562,708 to Combs et al, ATP works by delivering a burst of pacing stimuli at an empirically chosen frequency at a single pacing site in order to stimulate the excitable gap of a reentrant circuit, disrupting and terminating the circuit.

The use of an alternative kind of ATP delivered from far-field electrodes and known as far-field overdrive pacing has been proposed for implantable devices as described, for example, in U.S. Pat. No. 5,265,600 to Adams et al., U.S. Pat. No. 5,676,687 to Ayers, U.S. Pat. No. 6,510,342 to Park et al, U.S. Pat. No. 6,813,516 to Ujhelyi et al., and U.S. Pat. Nos. 7,079,891 and 7,113,822 to Kroll. U.S. Pat. No. 5,676,687 to Ayers and U.S. Pat. No. 6,185,459 to Mehra et al both describe an overdrive pacing arrangement that is delivered from near-field electrodes instead of far-field electrodes. The overdrive pacing arrangement is described in these patents as being used in conjunction with conventional kinds of defibrillation therapy where the overdrive pacing is utilized to prevent the recurrence of an AF.

Although ATP can be effective for slower AFls, the effectiveness of ATP can diminish for CLs below about two hundred milliseconds ("ms") and can be ineffective for faster AFl and AF. ATP failure can occur when the pacing lead is located at a distance from the reentrant circuit and the pacing-induced wavefront is annihilated before reaching the circuit. This can be a highly probable scenario for faster arrhythmias. In addition, the continued application of far-field ATP is known to potentially induce ventricular fibrillation, although the timing of the delivery of ATP can reduce the potential for inducing ventricular fibrillation and potential recurrence of AF as described, for example, in U.S. Pat. No. 6,091,991 to Warren, U.S. Pat. No. 6,847,842 to Rodenhiser et al., U.S. Pat. No. 7,110,811 to Wagner et al., and U.S. Pat. No. 7,120,490 to Chen et al.

Another manner in which atrial arrhythmias have been treated is with standard external defibrillators with the patient sedated during delivery of a defibrillation shock. There have also been external defibrillation systems, such as that disclosed in U.S. Pat. No. 5,928,270 to Ramsey, specifically designed for use with atrial arrhythmias. However, in order to provide an external shock that can effectively terminate arrhythmias with electrode placed externally on the body, such systems must provide higher energy shocks than would be required by implantable devices. In addition, externally applied shocks necessarily recruit more of the skeletal musculature resulting in potentially more pain and discomfort to the patient.

Another method of treatment for patients with recurrent persistent AF is the implantable atrial defibrillator ("IAD"), such as described in U.S. Pat. No. 3,738,370 to Charms, and U.S. Pat. No. 3,942,536 to Mirowski. Although initial clinical trials have shown that IADs have a high specificity and sensitivity to AF and deliver safe and effective shocks, the energy level needed for successful cardioversion can exceed the pain threshold. Endocardial cardioversion shock energies greater than 0.1 J are perceived to be uncomfortable (Ladwig, K. H., Marten-Mittag, B., Lehmann, G., Gundel, H., Simon, H., Alt, E., Absence of an Impact of Emotional Distress on the Perception of Intracardiac Shock Discharges, International Journal of Behavioral Medicine, 2003, 10(1): 56-65), and patients can fail to distinguish energy levels higher than this and find them equally painful. The pain threshold depends on many factors, including autonomic tone, presence of drugs, location of electrodes and shock waveforms. Moreover, pain thresholds can be different from patient to patient.

Various approaches have sought to lower the energy level required for effective atrial fibrillation. A number of systems, such as, for example, U.S. Pat. No. 5,282,836 to Kreyenhagen et al., U.S. Pat. No. 5,797,967 to KenKnight, U.S. Pat. Nos. 6,081,746, 6,085,116 and 6,292,691 to Pendekanti et al., and U.S. Pat. No. 6,556,862 and U.S. Pat. No. 6,587,720 to Hsu et al. disclose application of atrial pacing pulses in order to lower the energy level necessary for atrial defibrillation shocks. The energy delivered by pacing pulses is relatively nominal in comparison to defibrillation shocks. U.S. Pat. No. 5,620,468 to Mongeon et al. discloses applying cycles of low energy pulse bursts to the atrium to terminate atrial arrhythmias. U.S. Pat. No. 5,840,079 to Warman et al. discloses applying low-rate ventricular pacing before delivering atrial defibrillation pulses. U.S. Pat. Nos. 6,246,906 and 6,526,317 to Hsu et al. disclose delivering both atrial and ventricular pacing pulses prior to delivering an atrial defibrillation pulse. U.S. Pat. No. 5,813,999 to Ayers et al. discloses the use of biphasic shocks for atrial defibrillation. U.S. Pat. Nos. 6,233,483 and 6,763,266 to Kroll discloses the use of multi-step defibrillation waveform, while U.S. Pat. No. 6,327,500 to Cooper et al. discloses delivering two reduced-energy, sequential defibrillation pulses instead of one larger energy defibrillation pulse.

Other systems have sought to lower the patient's perception of the pain associated with atrial defibrillation shocks. For example, U.S. Pat. No. 5,792,187 to Adams applies electromagnetic stimulation of nerve structures in the area of the shock to block the transmission of the pain signal resulting from the shock. U.S. Pat. No. 6,711,442 to Swerdlow et al. and U.S. Pat. Nos. 7,155,286 and 7,480,351 to Kroll et al. disclose application of a "prepulse" prior to application of a high voltage shock pulse in order to reduce the perceived pain and startle response caused by the shock pulse. U.S. Pat. No. 5,925,066 to Kroll et al. discloses a drug delivery system in combination with anti-tachy pacing for inhibiting pain upon detection of atrial fibrillation. U.S. Pat. No. 7,142,927 to Benser measures the physical displacement of an unconscious patient in response to various shock levels and programs an arrhythmia treatment device to provide shocks that will not cause an excessive level of discomfort.

Despite these efforts, there remains a need for improved atrial arrhythmia treatment methods and devices enabling successful electrical treatment without exceeding the pain threshold of any given patient and without relying on pharmacological or ablative treatments.

SUMMARY OF THE INVENTION

Embodiments of methods and apparatus in accordance with the present disclosure provide for a three-stage atrial cardioversion therapy to treat atrial arrhythmias within pain tolerance thresholds of a patient. An atrial arrhythmia treatment in accordance with various embodiments includes an implantable therapy generator adapted to generate and selectively deliver a three-stage atrial cardioversion therapy and at least two leads operably connected to the implantable therapy generator, each lead having at least one electrode adapted to be positioned proximate the atrium of a heart of the patient. The atrial arrhythmia treatment device is programmed with a set of therapy parameters for delivering a three-stage atrial cardioversion therapy to a patient via both a far-field configuration and a near-field configuration of the electrodes upon detection of an atrial arrhythmia by the atrial arrhythmia treatment device.

The three-stage atrial cardioversion therapy includes a first stage for unpinning of one or more singularities associated with an atrial arrhythmia, a second stage for anti-repinning of the one or more singularities associated with the atrial arrhythmia, and a third stage for extinguishing of the one or more singularities associated with the atrial arrhythmia. In various embodiments, the first stage comprises two to ten far-field atrial cardioversion pulses of more than 10 volts and less than 100 volts. In one such embodiment, the first stage comprises two biphasic pulses with a voltage amplitude ranging from 10 volts to 30 volts. Pulse duration may be less than 10 milliseconds and a pulse coupling interval ranges 20 to 50 milliseconds, and the first stage has a total duration of less than two cycle lengths of the atrial arrhythmia and is triggered in relation to an R-wave and delivered within a ventricular refractory period with an energy of each biphasic atrial cardioversion pulse less than 0.1 joules.

In an embodiment, the second stage comprises five to ten far field pulses of ultra-low energy monophasic pulses with a pulse duration of more than 5 and less than 20 milliseconds and a pulse coupling interval of between 70-100% of the cycle length of the atrial arrhythmia. In one such embodiment, the second stage comprises six monophasic shocks of one volt to three volts.

In an embodiment, the third stage comprises five to ten near field pulses with a pulse duration of more than 0.2 and less than 5 milliseconds and a pulse coupling interval of between 70-100% of the cycle length of the atrial arrhythmia. In one such embodiment, the third stage pulses are paced at 88% of the atrial fibrillation cycle length and at three times the near-field atrial capture threshold. The three-stage atrial cardioversion therapy is delivered in response to detection of the atrial arrhythmia with each stage having an inter-stage delay of between 50 to 400 milliseconds and in some embodiments, without confirmation of conversion of the atrial arrhythmia until after delivery of the third stage.

In various embodiments, an atrial arrhythmia treatment apparatus includes at least one electrode adapted to be implanted proximate an atrium of a heart of a patient to deliver far field pulses and at least one electrode adapted to implanted proximate the atrium of the heart of the patient to deliver near field pulses and sense cardiac signals. An implantable therapy generator is operably connected to the electrodes and includes a battery system operably coupled and providing power to sensing circuitry, detection circuitry, control circuitry and therapy circuitry of the implantable therapy generator. The sensing circuitry senses cardiac signals representative of atrial activity and ventricular activity. The detection circuitry evaluates the cardiac signals representative of atrial activity to determine an atrial cycle length and detect an atrial arrhythmia based at least in part on the atrial cycle length. The control circuitry, in response to the atrial arrhythmia, controls generation and selective delivery of a three-stage atrial cardioversion therapy to the electrodes with each stage having an inter-stage delay of 500 to 400 and without confirmation of conversion of the atrial arrhythmia during the three-stage atrial cardioversion therapy. The therapy circuitry is operably connected to the electrodes and the control circuitry and includes at least one first stage charge storage circuit selectively coupled to the at least one far field electrode that selectively stores energy for a first stage of the three-stage atrial cardioversion therapy, at least one second stage charge storage circuit selectively coupled to the at least one far field electrode that selectively stores a second stage of the three-stage atrial cardioversion therapy, and at least one third stage charge storage circuit selectively coupled to the near field electrode that selectively stores a third stage of the three-stage cardioversion therapy.

The methods and devices of the present disclosure can exploit a virtual electrode polarization ("VEP") enabling successful treatment of AF and AFl with an implantable system without exceeding the pain threshold of any given patient. This is enabled by far-field excitation of multiple areas of atrial tissue at once, rather than just one small area near a pacing electrode, which can be more effective for both AFl and AF. The methods can differ from conventional defibrillation therapy, which typically uses only one high-energy (about one to about seven joules) monophasic or biphasic shock or two sequential monophasic shocks from two different vectors of far-field electrical stimuli. To account for pain threshold differences in patients, a real-time feedback to the patient can be provided in estimating the pain threshold during the calibration and operation of the implantable device.

The methods and devices of embodiments of the present disclosure can utilize a low-voltage phased unpinning far-field therapy together with near-field therapy that forms the three-stage atrial cardioversion therapy to destabilize or terminate the core of mother rotor, which anchors to a myocardial heterogeneity such as the intercaval region or fibrotic areas. A significant reduction in the energy required to convert an atrial arrhythmia can be obtained with this unpinning, anti-repinning and then extinguishing technique compared with conventional high-energy defibrillation, thus enabling successful cardioversion without exceeding the pain threshold of a patient.

Applying far-field low energy electric field stimulation in an appropriate range of time- and frequency-domains can interrupt and terminate the reentrant circuit by selectively exciting the excitable gap near the core of reentry. By stimulating the excitable gap near the core of the circuit, the reentry can be disrupted and terminated. The reentrant circuit is anchored at a functionally or anatomically heterogeneous region, which constitutes the core of reentry. Areas near the heterogeneous regions (including the region of the core of reentry) will experience greater polarization in response to an applied electric field compared with the surrounding, more homogeneous tissue. Thus, the region near the core of reentry can be preferentially excited with very small electric fields to destabilize or terminate anchored reentrant circuits. Once destabilized, subsequent shocks can more easily terminate the arrhythmia and restore normal sinus rhythm.

Virtual electrode excitation can be used at local resistive heterogeneities to depolarize a critical part of the reentry pathway or excitable gap near the core of reentry. Various pulse protocols for a three-stage atrial cardioversion therapy to terminate atrial arrhythmias in accordance with aspects of the present invention are contemplated. In one aspect, the reentry is either terminated directly or destabilized by far-field pulses delivered in a first and second stage and then terminated by additional stimuli by near-field pulses delivered in a third stage of the three-stage atrial cardioversion therapy. The low energy stimulation can be below the pain threshold and, thus, may cause no anxiety and uncomfortable side effects to the patient. In another aspect, a phased unpinning far-field therapy can be delivered in response to a detected atrial arrhythmia, with post treatment pacing administered as a follow-up therapy to the phased unpinning far-field therapy.

To further optimize this low energy method of termination, multiple electric field configurations can be used to optimally excite the excitable gap near the core of reentry and disrupt the reentrant circuit. These field configurations can be achieved by placing several defibrillation leads/electrodes into the coronary sinus (with both distal and proximal electrodes), the right atrial appendage, and the superior venae cavae. In another embodiment, an electrode can be placed in the atrial septum. Electric fields can be delivered between any two or more of these electrodes as well as between one of these electrodes and the device itself (hot can configuration). In another aspect, segmented electrodes with the ability to selectively energize one or more of the electrode segments can be used. Modulation of the electric field vector can then be used to achieve maximum coverage of the entire atria within one set of shock applications or on a trial to trial basis. The optimal electric fields used and the correct sequence of fields can also be explored on a trial and error basis for each patient.

In another aspect of the present invention, a pain threshold protocol is implemented for the treatment. The device and a plurality of leads are implanted into a patient who is sedated or under anesthesia. When the patient is completely free from the effects of the sedation or anesthetic, the device is instructed to individually interrogate the implanted leads, with stimulation being activated between both the leads and also between the can and the leads. The patient is asked to indicate a level of discomfort for each stimulation. The stimulation energy is initially set at low values and then is increased in a ramp-up mode, and the patient is asked to indicate when their pain threshold is reached. Default maximum stimulation energy levels previously stored in the device are replaced by the custom values determined through this protocol, and the device is programmed to restrict therapy to energy levels that are below these custom values.

In another aspect of the present invention, pre-treatment external information from a variety of sources, e.g. an electrocardiogram or a magnetic resonance image of the patient, regarding the likely location of a reentrant loop can be used to facilitate certain aspects of the treatment. Such external information can be used to determine the suitability of a patient for the procedure, vis-a-vis alternate treatments such as ablation or drug therapy, and to determine lead selection and placement, or determine the initial lead energizing pattern.

In another aspect of the present invention, the morphology of an electrogram of an arrhythmia can be documented, stored, and compared to previously stored morphologies. Anatomic location(s) of the reentry circuit(s) may be determined by the specific anatomy and physiological remodeling of the atria, which are unique for each patient. The embodiment takes advantage of the observation that several morphologies of atrial arrhythmias tend to occur with higher frequency than others. Optimization of electric field configuration and pulse sequence of the therapy may be conducted separately for each electrogram morphology and stored in memory for future arrhythmia terminations. When an arrhythmia is detected, it will be determined whether the morphology of the electrogram of an arrhythmia is known. If it is, the optimized therapy stored in memory may be applied to convert that arrhythmia.

In an aspect of the present invention, a method for destabilization and termination of atrial tachyarrhythmia includes detecting an atrial tachyarrhythmia initiation from sensing of atrial electrical activity, estimating a minimum or dominant arrhythmia cycle length (CL), sensing ventricular electrical activity to detect a ventricular R-wave, delivering far-field atrial electrical shocks/stimulation as a pulse train from two to ten pulses during one or several cycles of AF/AFl, optionally delivering atrial pacing with CL generally from about 70% to about 100% of sensed atrial fibrillation cycle length ("AFCL") minimum value, and (a) determining ventricular vulnerable period using R-wave detection to prevent or inhibit induction of ventricular fibrillation by atrial shock, (b) determining the atrial excitation threshold by applying electrical shock through different implanted atrial defibrillation leads and subsequently sensing for atrial activation, (c) determining pain threshold by a feedback circuit that uses information provided by the patient during both the implantation and calibration procedure, and during the execution of the device learning algorithms, (d) determining the ventricular far-field excitation threshold by applying electrical shock through different implanted atrial defibrillation leads and subsequently sensing for ventricular activation, (e) delivering far-field stimuli to the atria by sequentially delivering several pulses at energies above the atrial excitation threshold.

In another aspect of the present invention, an implantable cardiac therapy device for treating an atrium in need of atrial defibrillation includes one or more sensors comprising one or more implanted electrodes positioned in different locations for generating electrogram signals, one or more pacing implanted electrodes positioned in different locations for near-field pacing of different atrial sites, one or more implanted defibrillation electrodes positioned in different locations for far-field delivery of electrical current, and an implantable or external device which can be capable to deliver a train of pulses.

In one exemplary embodiment, the implantable device is implanted just under the left clavicle. This location places the device in approximate alignment with the longitudinal anatomical axis of the heart (an axis through the center of the heart that intersects the apex and the inter-ventricular septum). When the electrodes are implanted in this manner, the arrangement of the device and electrodes is similar in configuration to the top of an umbrella: the device constituting the ferrule of an umbrella, and the electrodes constituting the tines of the umbrella. The electrodes of the device are energized in sequential order to achieve electrical fields of stimulation that is similar to "stimulating" the triangles of umbrella fabric, one after the other, in either a clockwise or counter-clockwise manner or in a custom sequence. In one aspect, a right ventricular lead is positioned as part of the implantation. In another aspect, no ventricular lead is positioned, removing the need for a lead to cross a heart valve during lead implantation. Leads may be active or passive fixation.

In another aspect, the device can be fully automatic; automatically delivering a shock protocol when atrial arrhythmias are detected. In another aspect, the device can have a manual shock delivery; the device prompting the patient to either have a doctor authorize the device to deliver a shock protocol, or the device can prompt the patient to self-direct the device to deliver a shock protocol in order to terminate a detected arrhythmia. In another aspect, the device can be semi-automatic; a "bed-side" monitoring station can be used to permit remote device authorization for the initiation of a shock protocol when atrial arrhythmias are detected.

BRIEF DESCRIPTION OF THE DRAWINGS

The invention may be more completely understood in consideration of the following detailed description of various embodiments of the invention in connection with the accompanying drawings, in which:

FIG. 1B depicts a schematic posterior view of a human heart and anatomical locations of implantable defibrillation leads and sensing electrodes with an optional lead placed in the right ventricle;

FIG. 3A is a photograph of a preparation of fluorescent optical mapping of the posterior atria during ACh-induced AFl and AF in a Langendorff perfused rabbit heart with a photodiode array optical mapping field of view;

FIG. 3B depicts activation maps and optical action potentials (OAP) during AFL and AF of FIG. 3A;

FIG. 5A depicts a simplified schematic posterior view of a human heart, anatomical locations of implantable defibrillation leads and electrodes, and the direction of a first shock/pulse train;

FIG. 5B depicts a simplified schematic posterior view of a human heart, anatomical locations of implantable defibrillation leads and electrodes, and the direction of a second shock/pulse train;

FIG. 5C depicts a simplified schematic posterior view of a human heart, anatomical locations of implantable defibrillation leads and electrodes, and the direction of a third shock/pulse train;

FIG. 8 provides a summary of shock amplitudes for six isolated canine right atria experiments in vitro;

FIGS. 25A-D depict a lead placement used to implement the three-stage therapy of FIG. 24 in the canine model;

Figure 1A:
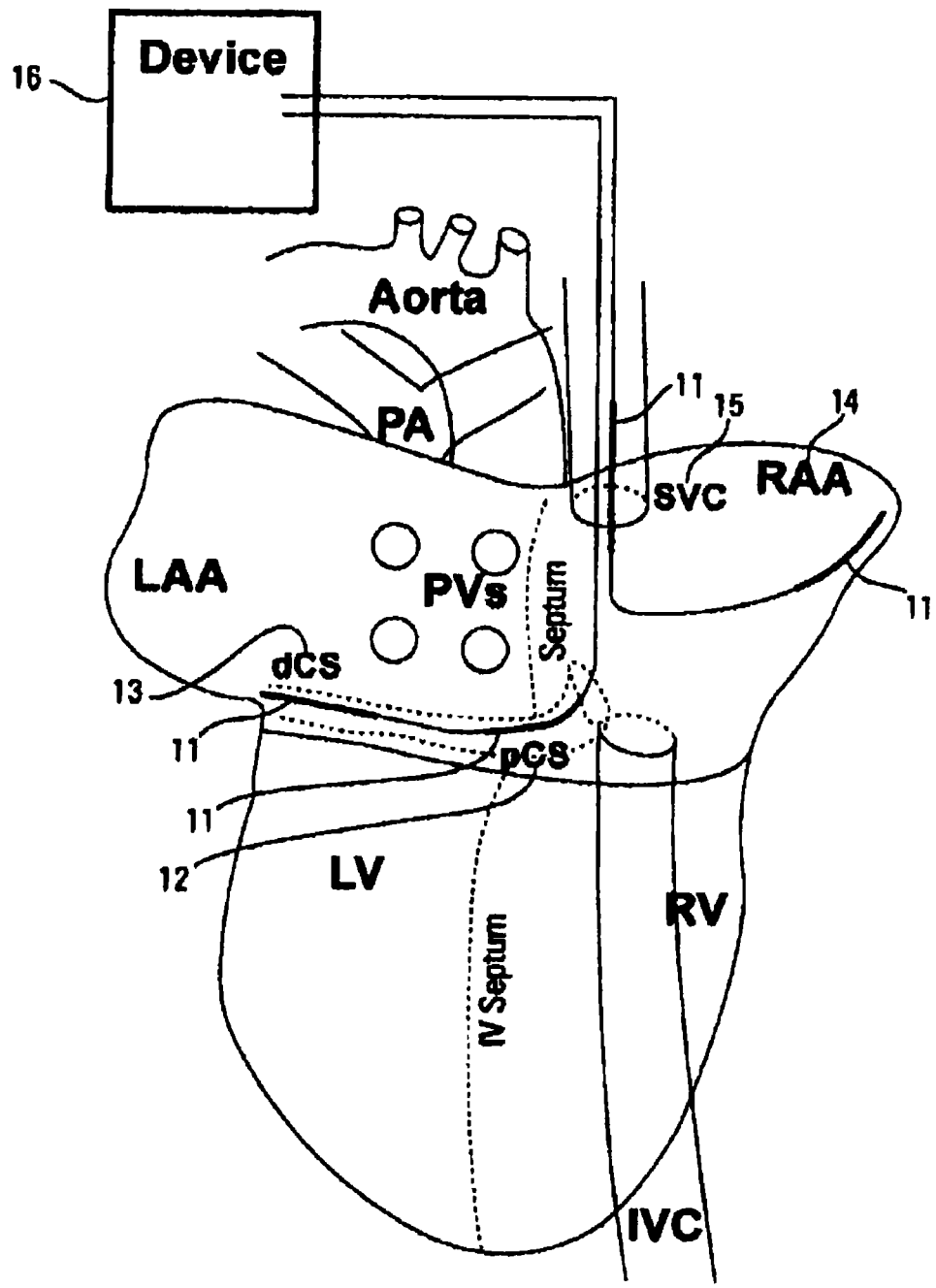
FIG. 1A depicts a schematic posterior view of a human heart and anatomical locations of implantable defibrillation leads and sensing electrodes.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Embodiments of the present disclosure are based on a low-voltage phased unpinning far-field therapy together with near-field therapy that forms the three-stage atrial cardioversion therapy for destabilizing and subsequently terminating anatomical reentrant tachyarrhythmias. A significant reduction in the energy required to convert an atrial arrhythmia can be obtained with this unpinning, anti-repinning and then extinguishing technique compared with conventional high-energy defibrillation, thus enabling successful cardioversion without exceeding the pain threshold of a patient.

The anatomical structure of cardiac tissue can be inherently heterogeneous. These syncytial heterogeneities of even modest proportions can represent a significant mechanism contributing to the far-field excitation process. Fishler, M. G., Vepa K., Spatiotemporal Effects of Syncytial Heterogeneities on Cardiac Far-field Excitations during Monophasic and Biphasic Shocks, Journal of Cardiovascular Electrophysiolgy, 1998, 9(12): 1310-24, which is incorporated herein by reference.

For purposes of the present application, the term "near-field," can relate to effects that are in close proximity to stimulating electrode(s), i.e., distances are restricted by several space constants (lambda) of cardiac tissue, which is typically up to several millimeters. Near-field effects can be strongly dependent upon distance from the electrodes. The term "far-field," on the other hand, can relate to effects that are generally independent or less dependent upon distance from the electrodes. They can occur at distances that are much greater than the space constant (lambda).

Applying far-field low energy electric field stimulation in a range of time- and frequency-domains can interrupt and terminate the reentrant circuit by selectively exciting the excitable gap near the core of reentry. High frequency far-field electric stimulation has significantly higher defibrillation success compared to near-field ATP. The reentrant circuit can be anchored at a functionally or anatomically heterogeneous region, which constitutes the core of reentry. The virtual electrode theory of myocardial excitation by electric field predicts that areas near the core will experience greater polarization in response to an applied electric field compared with the surrounding, more homogeneous tissue. Various shock protocols to terminate atrial arrhythmias are contemplated. Thus, in one aspect, the region near the core of reentry can be preferentially excited with very small electric fields to destabilize or terminate anchored reentrant circuits. Once destabilized, subsequent shocks can more easily drive the rotors away to the boundary of atrial tissue and restore normal sinus rhythm.

In traditional high-voltage defibrillation therapy, a truncated exponential biphasic waveform has a lower defibrillation energy as compared to monophasic shocks. However, in the case of phased unpinning far-field therapy ("PUFFT"), the use of multiple monophasic versus multiple biphasic waveforms was recently found to be more effective in terminating ventricular tachycardias in a rabbit model. This difference was thought to exist because optimal biphasic defibrillation waveforms may not produce VEPs because of an asymmetric effect of phase reversal on membrane polarization. Efimov, I. R., Cheng, Y., Van Wagoner, D. R., Mazgalev, T., Tchou, P. J., Virtual Electrode-Induced Phase Singularity: A Basic Mechanism of Defibrillation Failure, Circulation Research, 1998, 82(8): 918-25, which is incorporated herein by reference. VEP is discussed further in Efimov, I. R., Cheng, Y. N., Biermann, M., Van Wagoner, D. R., Mazgalev, T. N., Tchou, P. J., Transmembrane Voltage Changes Produced by Real and Virtual Electrodes During Monophasic Defibrillation Shock Delivered by an Implantable Electrode, Journal of Cardiovascular Electrophysiolgy, 1997, 8(9): 1031-45; Cheng, Y. N., Mowrey, K. A., Van Wagoner, D. R., Tchou, P. J., Efimov, I. R., Virtual Electrode-Induced Reexcitation: A Mechanism of Defibrillation, Circulation Research, 1999, 85(11):1056-66; and Fishier, M. G., Syncytial Heterogeneity as a Mechanism Underlying Cardiac Far-Field Stimulation During Defibrillation-Level Shocks. Journal of Cardiovascular Electrophysiolgy, 1998, 9(4): 384-94, all of which are incorporated herein by reference.

The ventricular defibrillation threshold ("DFT") can be significantly decreased by an orthogonally rotating current field. Tsukerman, B. M., Bogdanov, Klu, Kon, M. V., Kriukov, V. A., Vandiaev, G. K., Defibrillation of the Heart by a Rotating Current Field, Kardiologiia, 1973, 13(12): 75-80, which is incorporated herein by reference. By combining two sequential shocks with a rotating electrical field vector, the atrial defibrillation threshold ("ADFT") of the standard lead configuration (right atrium to distal coronary sinus) can be significantly reduced when followed by a second shock along the atrial septum delivered between electrodes in the proximal coronary sinus and either the SVC or Bachmann's bundle. Zheng, X., Benser, M. E., Walcott, G. P., Smith, W. M., Ideker, R. E., Reduction of the Internal Atrial Defibrillation Threshold with Balanced Orthogonal Sequential Shocks, Journal of Cardiovascular Electrophysiolgy, 2002; 13(9): 904-9, which is incorporated herein by reference. The ADFT can be further reduced with balanced sequential shocks.

Virtual electrode excitation can be used at local resistive heterogeneities to depolarize a critical part of the reentry pathway or excitable gap near the core of reentry. Thus, reentry can be terminated directly or destabilized and then the reentry can be terminated by additional stimuli. This technique can be exploited in an implantable or external device, which, upon sensing an atrial tachyarrhythmia, can apply the low energy stimulation at several different timing intervals until the correct timing can be achieved and the arrhythmia can be terminated. This "trial and error" approach can be used, as atrial arrhythmias are not immediately life threatening. Also, the low energy stimulation can be expected to be below the pain threshold and thus may cause no anxiety and uncomfortable side effects to the patient.

To further optimize the low energy method of termination, multiple electric field configurations can be used to optimally excite the excitable gap near the core of reentry and disrupt the reentrant circuit. Referring to FIGS. 1A and 1B, these field configurations can be achieved by placing several implantable defibrillation electrodes 11 into the proximal 12 and distal 13 coronary sinus ("CS"), the right atrial appendage ("RAA") 14, and the superior venae cavae ("SVC") 15. In one aspect, a right ventricular lead is positioned as part of the implantation (FIG. 1B). In another aspect, no ventricular lead is positioned (FIG. 1A), removing the need to cross a heart valve during lead implantation. Leads may be active or passive fixation. As can be seen from FIG. 1, no leads are placed in the left side of the heart, thus reducing the time required for implantation.

Electric fields can be delivered between any two of these electrodes as well as between one of these electrodes and the device itself 16 (hot can configuration). Modulation of the electric field vector can be used to achieve maximum coverage of the entire atria and to maintain optimal Virtual Electrode Polarization pattern through the entire cycle of arrhythmia in order to depolarize the maximum area of excitable gaps. The optimal electric fields used and the correct sequence of fields can also be explored on a trial and error basis for each patient or can be estimated based on external information regarding potential sites of the reentrant circuits, or can be based on a combination of both.

Figure 1C:
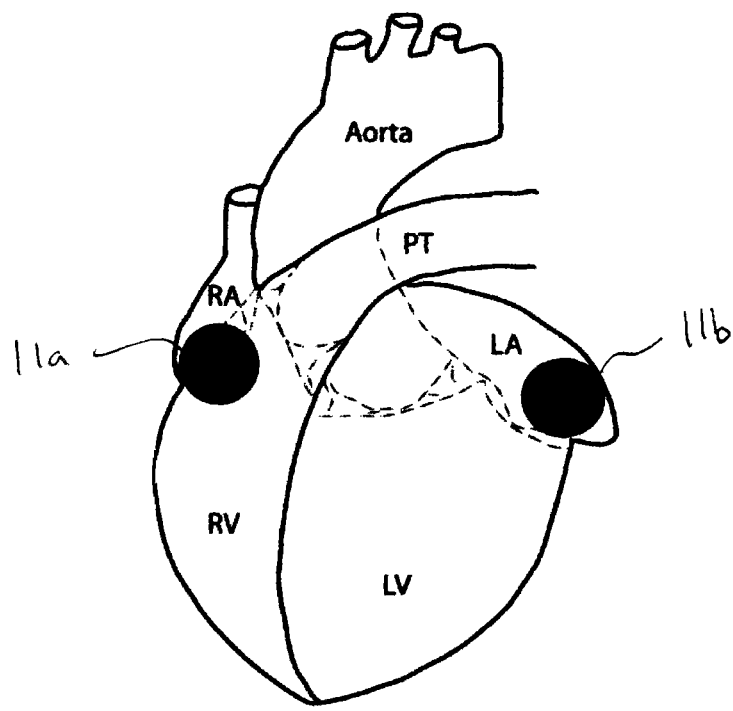
FIG. 1C depicts a schematic anterior view of a human heart and anatomical locations of implantable defibrillation leads and sensing electrodes with leads placed in the right and left atria.

Referring also to FIG. 1C, a first electrode 11a is placed in the right atrium, and a second electrode 11b is placed in the left atrium for delivery of atrial defibrillation therapy. Although only two electrodes 11a and 11b are depicted, it will be understood that additional electrodes and corresponding leads may also be implanted, including a ventricular sensing electrode, as well as other electrodes depicted and described with respect to FIGS. 1A and B.

FIGS. 5A, 5B and 5C together depict a clock-wise rotation of the vectors of a series of three consecutive far field unpinning shocks. In this example, multiple, monophasic shocks can be applied with intervals as a function of arrhythmia cycle length. In one example, the far field unpinning shocks can be square waves, 10 ms in duration of which the voltage and vectors will be varied to determine minimum termination voltage. In other embodiments, the far field unpinning shocks or pulses may be rounded, staggered, ascending, descending, biphasic, multiphasic or variations thereof.

In FIG. 5A a first far field unpinning shock 40 is applied between the electrode located in the right atrial appendage (b) and the device (a). In FIG. 5B a second far field unpinning shock 42 is applied between the electrode located distal in the coronary sinus (e) and the electrode located in the superior venae cavae (c). In FIG. 5C a third far field unpinning shock 44 is applied between the device (a) and the electrode located proximal in the coronary sinus (d).

Figure 5D:
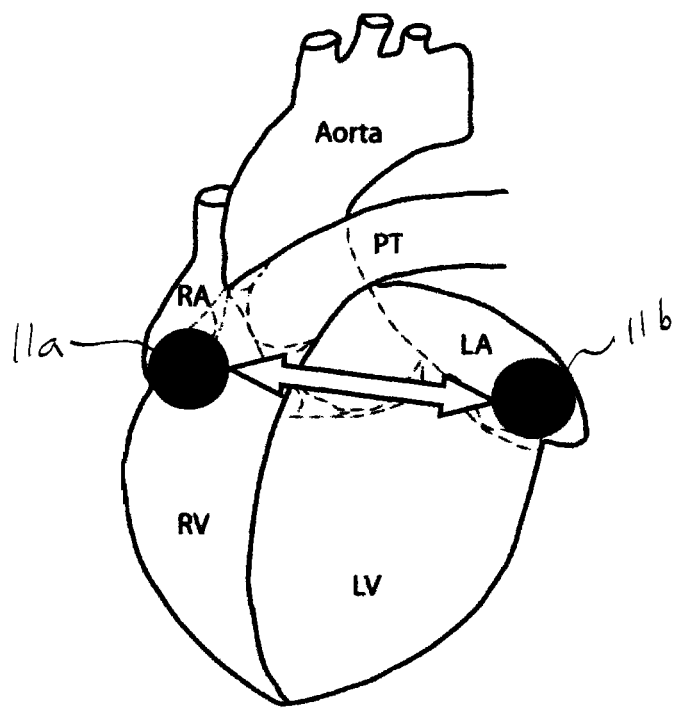
FIG. 5D depicts a simplified schematic anterior view of a human heart, anatomical locations of implantable defibrillation leads and electrodes, and directions of another shock/pulse train.

Referring also to FIG. 5D, shocks may also be applied between electrodes 11a in the right atrium and 11b in the left atrium, as indicated by the bi-directional arrow depicted. Although only two electrodes are depicted, and only a first electrical field vector from electrode 11a to 11b, and a second vector from electrode 11b to 11a are depicted, it will be understood that any series of shocks or pulses may be applied between electrodes 11a and 11b and other placed electrodes, including between electrodes 11a/11b and the device, to deliver a series of shocks between electrodes and the device as depicted and described above with respect to FIGS. 5A to 5C.

While a number of lead and electrode placements are described above, generally speaking, an optimal electrode configuration is one that maximizes current density across the atria, particularly in the region where the arrhythmia arises, thereby maximizing depolarization in the atrial region originating the arrhythmia.

An algorithm may be used for treatment of AFl and AF. To determine whether the atria are in flutter or fibrillation, the device can first estimate the CL of arrhythmia. For example, if the average atrial cardiac CL is less than 250 ms, but greater than 150 ms, the atria are considered to be in AFl. The distinguishing characteristics of AF and AFl vary on a patient-to-patient basis and thus these CL parameters can be programmable based on patient's need. Examples of distinguishing AF from AFl are described in U.S. Pat. No. 5,814,081, which is incorporated herein by reference. In addition, an algorithm can be used to characterize and categorize morphologies of atrial electrogram in order to use this information for patient-specific and morphology-specific optimization of phased unpinning far-field therapy.

An optimum time to apply the phased unpinning far-field therapy relative to the cardiac cycle may be determined from the ventricular sensing electrodes including RV or far-field R-wave wave detection. Examples of finding unsafe times for far-field shock are also described in U.S. Pat. No. 5,814,081.

Other timing considerations, particularly with respect to phase or stage durations, may be determined in whole or in part by characteristics of the sensed atrial fibrillation. As will be described below, while ventricular activity, such as R-wave characteristics, may be used to determine an overall therapy timing, such as a maximum window of time for therapy delivery, an AF CL may determine a particular phase duration within that window of time.

Learning algorithms may also used to optimize therapy on subsequent terminations. Once the optimal timing and field settings are achieved for a patient to terminate an atrial tachyarrhythmia, these settings are the starting point for termination of the next bout of AFl/AF.

Because AFl/AF are not immediately life-threatening arrhythmias, therapy can be optimized using a trial and error approach combined with learning algorithms to tailor therapy for each patient. The optimization includes two objectives: (a) terminating arrhythmia and (b) avoiding intensities associated with pain.

As described above, the pain threshold depends on many factors, including autonomic tone, presence of drugs, location of electrodes and shock waveforms. A value of 0.1 J has been reported by Ladwig, K. H., Marten-Mittag, B., Lehmann, G., Gundel, H., Simon, H., Alt, E., Absence of an Impact of Emotional Distress on the Perception of Intracardiac Shock Discharges, International Journal of Behavioral Medicine, 2003, 10(1): 56-65, which is incorporated herein by reference, as the energy value where pain and/or discomfort is first generally experienced. However, it can be different from patient to patient. Thus, a real-time feedback to the patient can be provided in estimating the pain threshold during either the implantation or calibration of the device or during execution of the optimizing learning algorithms.

Figure 6:
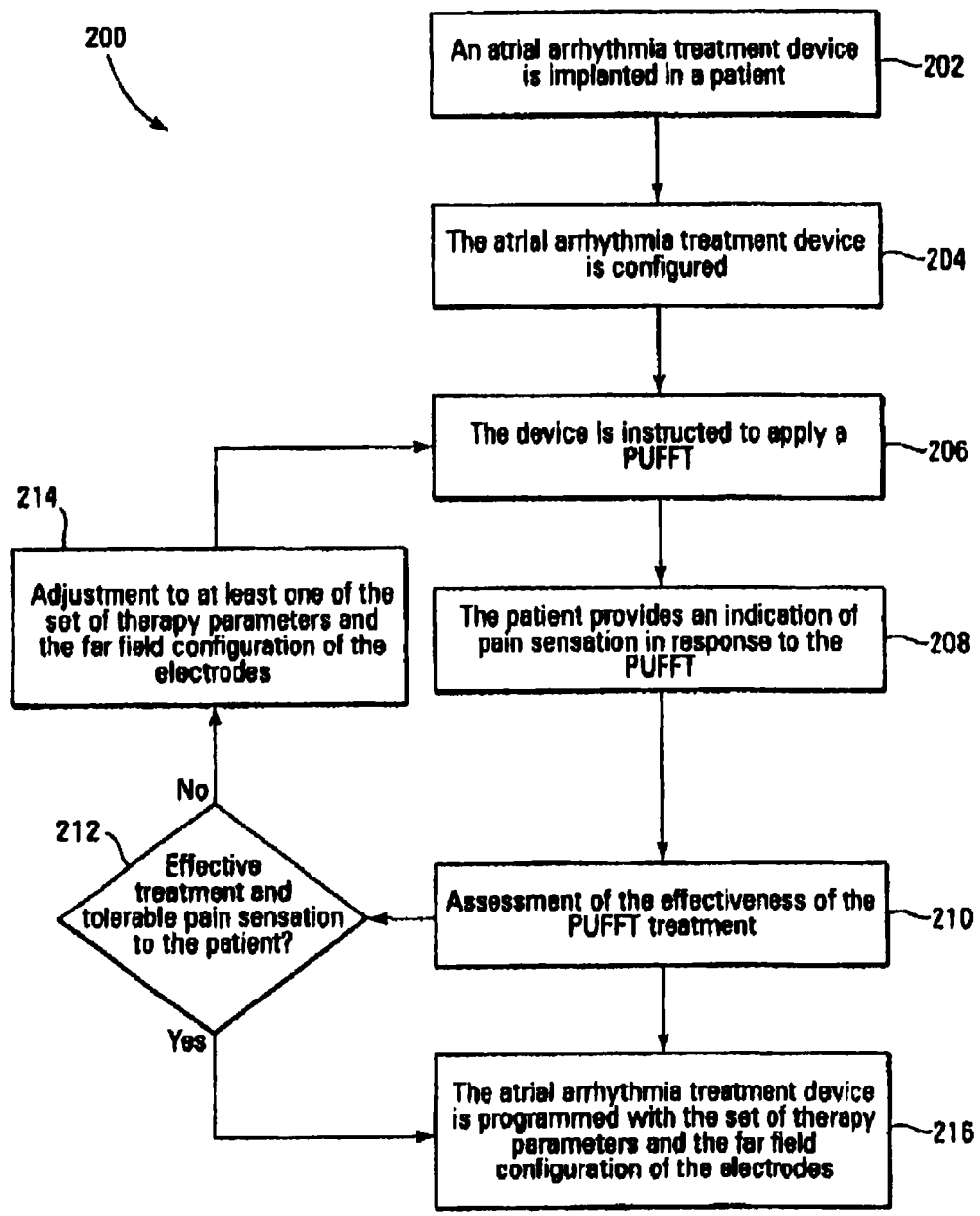
FIG. 6 depicts a flow chart illustrating a treatment method of an embodiment of the present disclosure.

Referring now to FIG. 6, a pain threshold protocol 200 is described. An atrial arrhythmia treatment device is implanted in a patient, who is sedated or under anesthesia, during a surgical procedure 202. The implanted device includes an implantable therapy generator and at least two leads operably connected to the implantable therapy generator, each lead having at least two electrodes adapted to be positioned proximate the atrium of a heart of the patient. At a time after completion of the surgical procedure, when the patient is fully conscious and completely free from the effects of the sedation or anesthetic, the atrial arrhythmia treatment device is configured 204. The device is instructed to apply a PUFFT treatment 206, via a far field configuration of the electrodes, to the patient in response to detection of an atrial arrhythmia, the PUFFT treatment having a first set of therapy parameters. The patient then provides an indication of pain sensation in response to the PUFFT 208. An assessment is made of the effectiveness of the PUFFT treatment of the atrial arrhythmia 210. An evaluation is made regarding the effectiveness of the PUFFT treatment and the indication of pain sensation 212. In response to both the indication of pain, and of the assessment of the effectiveness of the treatment, an adjustment is made to at least one of the set of therapy parameters and the far field configuration of the electrodes 214. Steps 206 to 212 are repeated until a set of therapy parameters and a far field configuration of the electrodes have been determined that provide an effective treatment of the atrial arrhythmia for the patient at a pain sensation that is tolerable to the patient. The atrial arrhythmia treatment device is then programmed with the set of therapy parameters and the far field configuration of the electrodes 216 as determined from steps 206-214 to be used by the device in automatically treating an atrial arrhythmia detected by the device.

Figure 2:
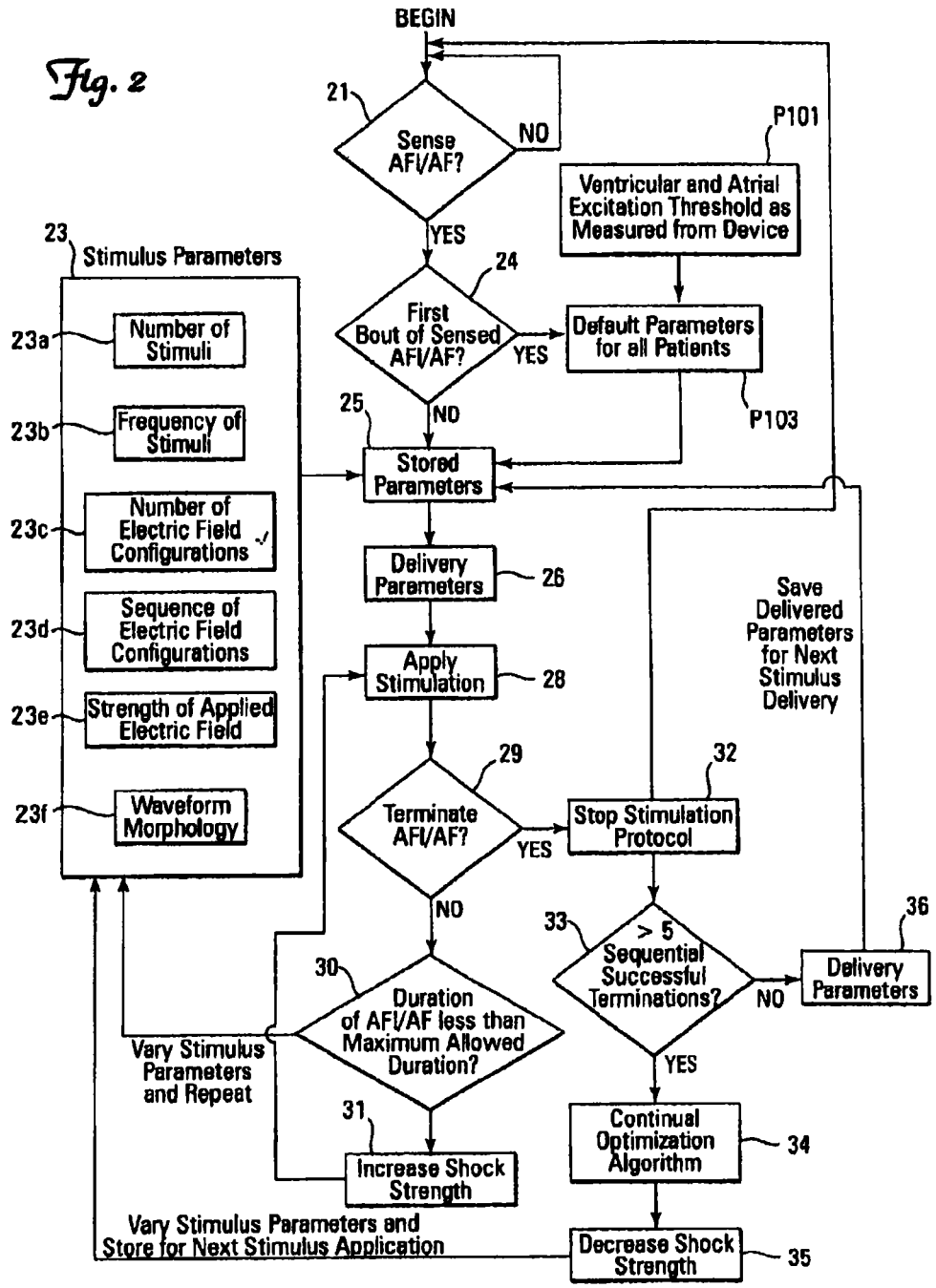
FIG. 2 is a flow chart illustrating a treatment method of an embodiment of the present disclosure.

Referring to FIG. 2, upon device implantation, several measurements are first made (P101-P103). The field excitation thresholds for both atrial and ventricular excitation are measured from each lead combination as described previously (P101). These values serve as the minimum and maximum stimulation strengths, respectively, and can be tested periodically by the device for changes. Stimulation strengths can also be increased until the patient senses the shock and feels pain. A patient feedback mechanism can be employed to register this maximum shock amplitude, which corresponds to pain threshold for this particular site. These minimum and maximum values outline the operating range of the device.

After implantation, the device enters a sensing mode (21) to sense for atrial tachyarrhythmias. When an arrhythmia is sensed, the minimum AFl/AF CL can be determined from all sensing electrodes. The minimum AFl/AF CL can then be used to calculate the stimulus frequency (23b), which may range from about 20% to about 100% of the minimum AFl/AF CL. As will be described further below, in some embodiments, a stimulus frequency is determined based on a range of 70% to 100% of AFl/AF CL, such that the time between shocks, or pulses, of a particular therapy phase or stage ranges from 70% to 100% of AFl/AF CL. The device then determines if the arrhythmia is the first bout of AFl/AF after implantation (24). If so, a default combination of stimulus parameters combined with the minimum stimulation strengths as previously measured can be used for the first defibrillation trial (P103) and (26). The combination of stimulus parameters (23) can include: number of stimuli (23a), frequency of stimuli (23b), number of electric field configurations (23c), sequence of electric field configurations (23d), field strength (23e), waveform morphology (23f), and the inter-stage delay. The default combination of parameters can be based on experimental evidence found in animal models of AFl/AF, previous experience with this technology, or results of patient specific testing at the time of implant. If it is not the first bout of AFl/AF after implant, stored parameters from the previous stimulus application can be used for the first defibrillation trial (25)-(26). In some embodiments, to avoid inducing a ventricular arrhythmia, the device then waits for the next sensed R-wave to deliver the atrial defibrillation therapy. The appropriate stimulus parameters are then delivered (28).

After the defibrillation trial, which may include multiple therapy stages, sensing can then be employed again to determine if the trial was successful (29). If the trial was unsuccessful, and the duration of AFl/AF has not exceeded the maximum allowed duration (30), the stimulus parameters (23) are varied and another defibrillation trial can be performed (25)-(29). Because of the large number of stimulus parameters (23), a neural network can be employed within the device to control the sequence and optimization of the parameters. The defibrillation trials continue (25)-(29) until the arrhythmia is terminated or until the maximum duration of AFl/AF is reached (30). Because prolonged AFl/AF can promote pathological remodeling of atria (atrial fibrillation begets atrial fibrillation), blood clotting and increase a patient's risk of stroke along with other complications, a higher energy rescue shock (31) can be delivered if necessary and low energy optimization can be continued upon the next bout of AFl/AF.

If a successful combination of parameters is found, the stimulus parameters can be saved (36), (25) and employed upon the next bout of AFl/AF. If a particular combination of stimulus parameters is found to be successful for many bouts of AFl/AF (i.e., >5 successful terminations) (33), the device can enter a "continual optimization algorithm" (34) to determine if the energy can be further decreased. The stimulus parameters can be varied at a lower energy (35), (23) to try to find another successful combination. If another such combination is not determined, the device can return to using the successful combination.

In one embodiment, the morphology of an arrhythmia's electrogram can be documented, stored, and compared to previously stored morphologies. Anatomic location(s) of the reentry circuit(s) are determined by the specific anatomy and physiological remodeling of the atria, which are unique for each patient. Thus, the morphologies can reveal the specific anatomic locations of the reentry circuits. Optimization of the pulse sequence of the therapy can be conducted separately for each electrogram morphology and stored in memory for future arrhythmia terminations.

Figure 9:
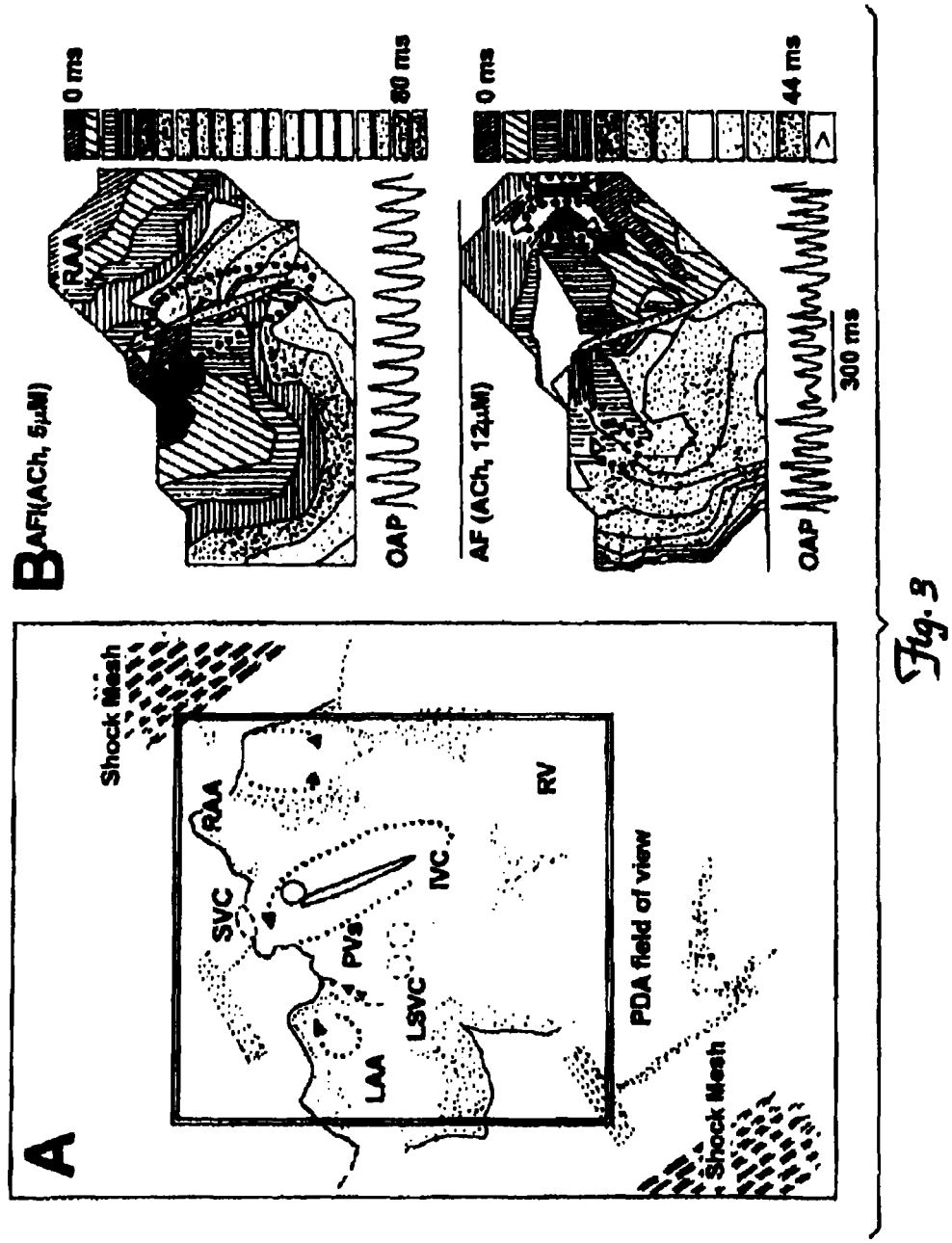
FIG. 9 provides a listing of potential electric field sequences for therapy provided to the regions in FIG. 7 by electrodes positioned as shown in FIGS. 5A, 5B and 5C.
Figure 7:
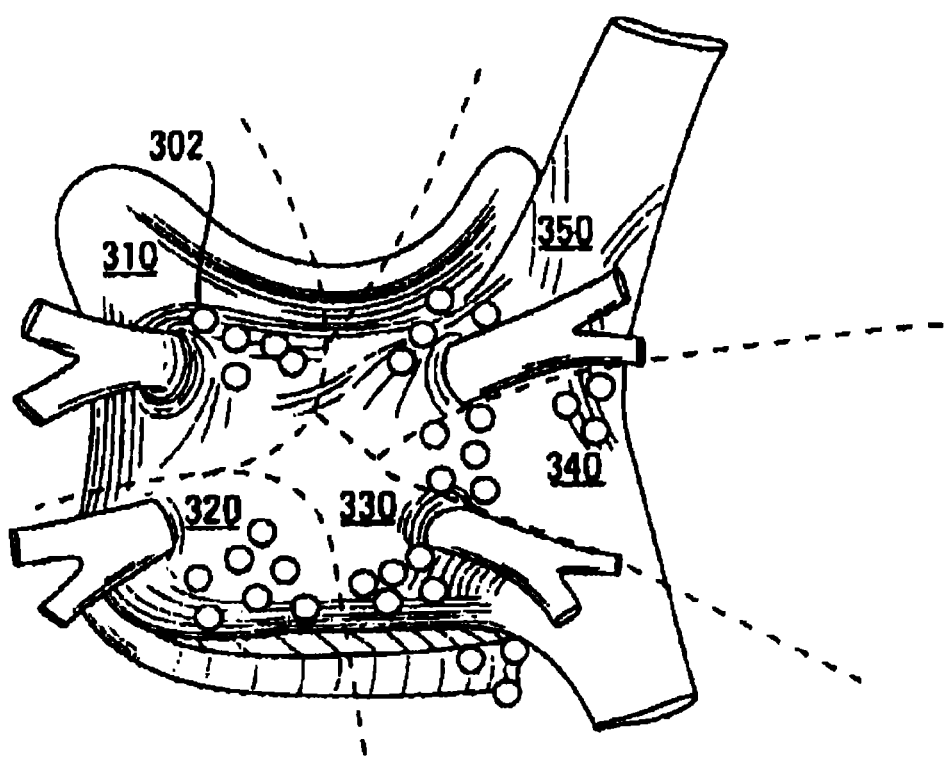
FIG. 7 depicts a simplified schematic view of a human heart showing potential locations of arrhythmias.

Referring to FIG. 7, various locations 302 where reentry circuits may be anchored are depicted. The locations 302 have been divided into five zones 310, 320, 330, 340 and 350 indicated by the dashed lines. In one embodiment, a default therapy sequence can be initiated for reentry circuits located in each zone. For example, if the morphology of the arrhythmia indicates that the reentry circuit is located in zone 310, the sequence of electric fields applied might begin between electrode (b) and electrode (a) (on the device) as depicted in FIG. 5A. The sequence may then continue with an electric field between electrode (e) and electrode (c) (FIG. 5B) followed by one between electrode (a) and electrode (d) (FIG. 5C). The table in FIG. 9 provides one example of potential default therapy sequences for each zone 310, 320, 330, 340, and 350 in FIG. 7. If the default therapy sequence in a given zone fails to terminate the arrhythmia, additional therapy sequences may subsequently be applied.

Because this device, in certain embodiments, can deliver a series of electric field stimuli in rapid succession, traditional implantable pulse generators, such as those normally used in ICDs generally may be inadequate for the device. Traditional implantable pulse generators employ a charging period (on the order of seconds) to charge a capacitor, then rapidly discharge the capacitor to apply the shock. Before the next shock application, the capacitor may need to be charged again. In this device, several low energy far field unpinning shocks/pulses (two-ten) can be applied in rapid succession (in some embodiments ranging from 10-100 ms apart, which in some embodiments is determined by the AFl/AF CL) for each unpinning shock.

The implantable pulse generator according to one type of embodiment of this device can include several smaller capacitors that charge before or during the defibrillation trials. For each stimulus delivered, a single capacitor discharges with the appropriate amount of energy followed sequentially by a discharge from another capacitor until the appropriate number of stimuli is delivered. The capacitors can all be charged simultaneously before the entire defibrillation trial or, alternatively, the capacitors can be charged sequentially in groups, or individually. In one example implementation, capacitors which are used for unpinning shocks that appear later in the defibrillation trial are charged while other unpinning shocks are applied earlier in the trial via other capacitors, which were charged previously. In a related example, a capacitor that is used for an earlier unpinning shock is re-charged during a subsequent one or more shock of the trial, and is further re-used for a later unpinning shock of the same trial. This latter example is facilitated in embodiments where the power supply is capable of sufficient current drive to charge the capacitors in sufficient time to permit their re-use within the same trial.

In a related embodiment, the device uses multiple capacitors for storing the electrotherapy energy, except that, unlike the example embodiment described above, each capacitor has sufficient energy storage to provide more than a single shock in the sequence.

In order to produce the appropriate stimuli across the appropriate lead configuration, a fast-switching network can be employed to switch the discharged energy between the different capacitors as well as switching the applied energy to the correct electrodes. The pretreatment of pulses is described further in U.S. Pat. Nos. 5,366,485 and 5,314,448, both of which are incorporated herein by reference.

Experimental Results

Referring to FIGS. 3A and 3B, a series of experiments were conducted in which the posterior epicardium of the right and left atria (RA and LA) and the pulmonary vein (PV) region of Langendorff-perfused rabbit hearts (n=9) were simultaneously optically mapped in control and during ACh perfusion (2.5-100 $\mu$M). In FIG. 3A, the fluorescent optical mapping of the posterior atria during ACh-induced AFl and AF in a Langendorff perfused rabbit heart with a photodiode array optical mapping field of view is shown wherein (1) the location of the origin of a normal sinus rhythm heart beat is indicated by a blue/purple circle, (2) the narrow gray oval indicates the line of intercaval conduction block, as identified during normal sinus rhythm and during pacing, the site of resistive heterogeneity, which is highly likely to serve as a pinning site for a reentry circuit during atrial flutter or atrial fibrillation, (3) dashed black lines with arrows indicate the location and direction of reentrant circuits, and (4) dashed white lines indicate vessels that have been ligated. In FIG. 3B, the activation maps and optical action potentials (OAP) during AFL and AF of FIG. 3A are shown, wherein (1) the narrow gray oval indicates the line of intercaval conduction block, the site of resistive heterogeneity, and (2) dashed white lines with arrows indicate the location and direction of reentrant circuits, and wherein isochronal maps are depicted in 4.0 ms steps.

Arrhythmias were provoked by a single premature stimulus or burst pacing. Low-energy shocks were delivered from two large mesh electrodes located on either side of the heart, oriented parallel to the vertical axis of the heart. To prevent or inhibit motion artifacts, Blebbistatin (BB) was used. BB is a highly specific inhibitor of myosin TI isoforms. Under control conditions, AF was not induced, and sustained AFl was induced only in 1 heart. ACh depressed the sinus rhythm and provoked atrial premature beats ("APBs") with a coupling interval of 93.+−.7 ms from the RA appendage, superior PVs and inferior vena cava regions. APBs resulted in spontaneous AF in 3 hearts. In 8 hearts, a single premature stimulus or burst pacing induced sustained AFl and AF (>10 min) at 7.+−.2 $\mu$M and 20.+−.8 $\mu$M ACh, respectively.

Referring again to FIG. 3B, AFl and AF were maintained by a single macroreentrant circuit around a region of conduction block between the SVC and IVC (CL=79.+−.10 ms) or multiple reentry circuits (CL=48.+−.6 ms), respectively. In most cases, AF was associated with mother rotor microreentry in the pectinate muscles of RA (75%) and/or LA (25%). FIG. 3B depicts an example of activation during AF. AF was associated with a stable mother rotor (figure-of-eight) in the RA appendage. Rarely, several complete rotations of an additional rotor were observed in the LA, but this rotor was generally not sustained.

To terminate the arrhythmias, monophasic five ms shocks were delivered from external mesh electrodes. Either a single shock was applied throughout various phases of AFl or multiple (three-five) shocks were applied within one AFl CL. Anti-tachycardia pacing (ATP, 8 pulses, 50-100% of AFl CL) was also applied from the RA appendage electrode or the IVC region electrode.

A statistically significant phase window was found in which single shocks terminated AFl with a defibrillation threshold (DFT) of 0.9.+−.0.4 V/cm. Termination of AFl was preceded by a short (<1 sec) run of AF in 30% of cases, which are demonstrated examples of destabilization of reentry before its complete termination. Multiple shocks had lower termination strength of 0.7.+−.0.1 V/cm. ATP alone terminated AFl in only 4 of the 6 hearts on which it was applied with 15% of terminations preceded by AF and 11% of applications resulting in sustained AF. Conventional time-independent monophasic shocks terminated sustained AF with a minimum strength 4.7.+−.0.9 V/cm only. The lower efficacy of ATP suggests that low-energy field stimulation may be an alternative to ATP for the treatment of AFl.

Figure 4:
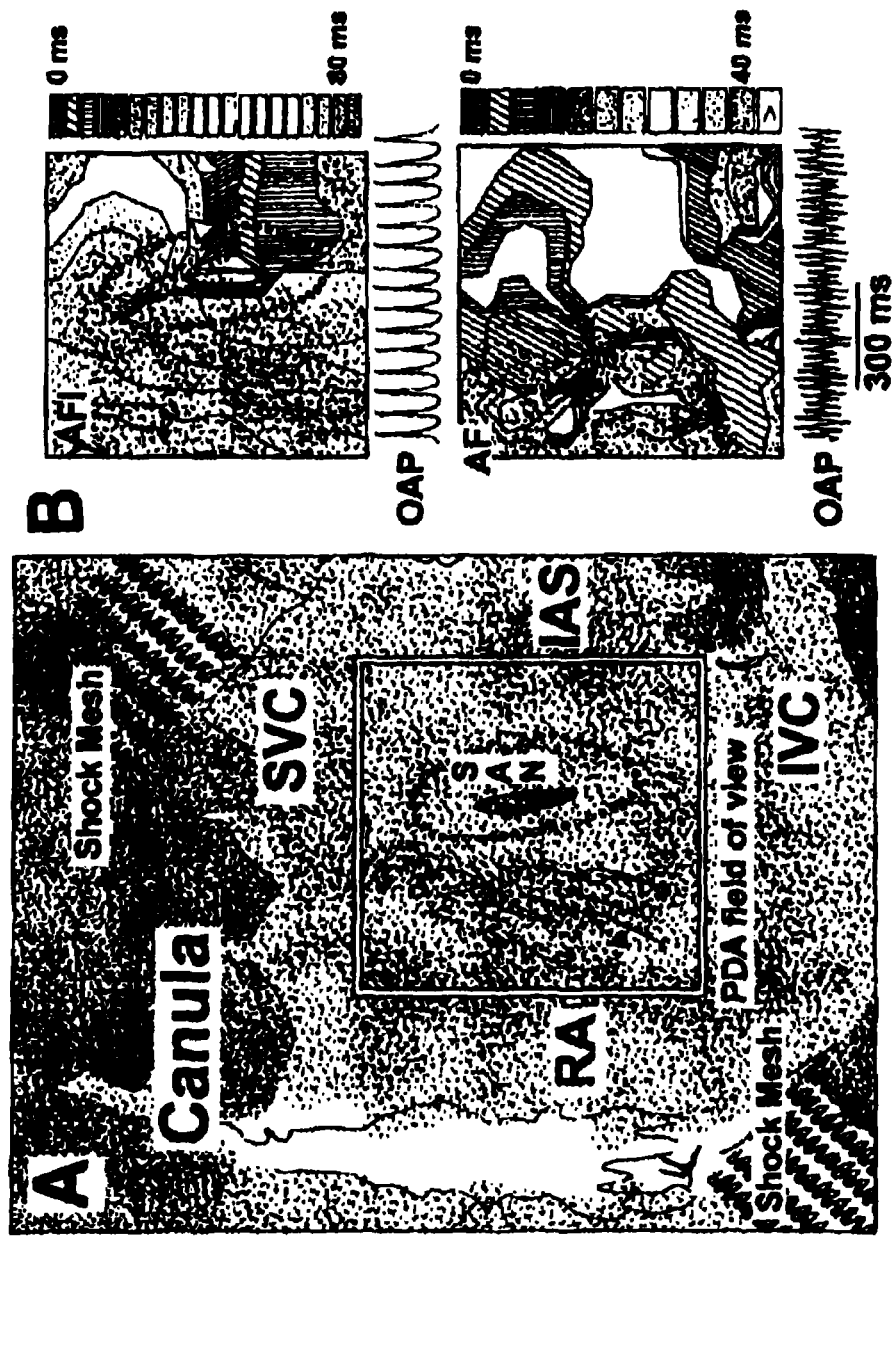
FIG. 4A is a photograph of a preparation of fluorescent optical mapping of the right atrial endocardium during ACh-induced AFl and AF in the canine isolated atria with a photodiode array optical mapping field of view.
FIG. 4B depicts activation maps and OAPs during AFL and AF of FIG. 4A.

Experimental protocols were transferred from the rabbit model to the canine AF model. AFl or AF was electrically induced in isolated, coronary-perfused canine right atria (n=7) in the presence of acetylcholine (3.8.+−.3.2 $\mu$M). CL of AFl and AF was 130.7.+−.30.7 ms and 55.6.+−.7.9 ms, respectively. Referring to FIGS. 4A and 4B, using optical mapping (16.times.16 photodiode array), AFl and AF were determined to be maintained by single macroreentrant circuits around the sinoatrial node region or multiple reentry circuits, respectively. FIG. 4A shows a preparation of fluorescent optical mapping of the right atrial endocardium during ACh-induced AFl and AF in the canine isolated atria with a photodiode array optical mapping field of view, wherein (1) the sin .theta.-atrial node, which is a resistive heterogeneity, and often serves as a pinning location for a reentry circuit during atrial flutter is indicated by a dark blue/purple oval, (2) dashed white lines with arrows indicate a reentry circuit during atrial flutter, and (3) dashed black lines with arrows indicate a reentry circuit during atrial fibrillation (which is pinned to another resistive heterogeneity). FIG. 4B shows activation maps and OAPs during AFL and AF wherein (1) dashed white lines with arrows indicate a reentry circuit during atrial flutter, and (2) dashed black lines with arrows indicate a reentry circuit during atrial fibrillation (which is pinned to another resistive heterogeneity). It can be seen that AF reentry cores were located at functional and anatomical heterogeneities in the pectinate muscles and SVC/IVC regions. Single or multiple monophasic 10 ms shocks were applied from parallel mesh electrodes in the tissue bath using the rabbit experimental setup.

The far-field diastolic threshold of excitation was reached at $0.14.+-.0.12$ V/cm $(0.005+0.0001$ J) when supra-threshold virtual cathodes were induced at local resistive heterogeneities. Single-shock ADFT was significantly lower for AFl vs. AF ($0.2.+-.0.06$ vs. $7.44.+-.3.27$ V/cm, or $0.018.+-.0.001$ vs. $2.6.+-0.0.78$ J; $p<0.05$). However, application of 2 or 3 pulses delivered at an optimal coupling interval between pulses allowed significant reduction of the ADFT for AF: $3.11.+-.0.74$ V/cm and $3.37.+-.0.73$ V/cm, or $0.44.+-.0.04$ and $0.48.+-.0.03$ J for 2 and 3 pulses, respectively ($p<0.05$ vs. 1 pulse). Coupling interval optimization was performed in the range of 20-190% of the AF CL. Optimal coupling interval was $87.3.+-.18.6$% and $91.3.+-.17.9$% for two and three pulses, respectively. The table in FIG. 8 provides the summary of these results collected in six canine atrial preparations.

Moreover, low voltage shocks (0.1-1 V/cm) converted AF to AFl. Thus, atrial defibrillation or cardioversion may best be achieved by a multi-step process that includes: (a) conversion of AF to AFL, and (b) termination of AFl. Both steps are achieved with multiple pulses with energy ranging from 0.02-0.1 J.

Similar ADFT values for AF and AFl were found in both models, demonstrating the relevance of the rabbit model for experiments in dogs and further applications. Lower ADFTs can be obtained when multiple field directions are used, as well as when appropriately timed shocks or multiple shocks are used.

The method described above is exemplary of a method in accordance with one aspect of the present invention. The methods above may be accomplished by an internal, implanted device. The methods above may be accomplished using any number and configuration of electrode arrangements, such as endocardial, epicardial, intravenous, implantable or external, or any combination thereof, to deliver electrical cardiac stimulation in accordance with the present invention. Multiple path electrode configurations as contemplated for use with some embodiments of the present as shown, for example, in U.S. Pat. Nos. 5,306,291 and 5,766,226, the disclosure of each of which are incorporated herein by reference.

It is contemplated that the method of the present invention can be utilized together with, or separate from, other pacing and defibrillation therapies. For example, the present invention can be implemented as part of an ICD where a high voltage defibrillation shock can be delivered in the event that the method of the present invention is unable to successfully convert a cardiac arrhythmia. Alternatively, the present invention could be implemented as part of a conventional pacemaker to provide for an emergency response to a VT/VF condition in the patient that would increase the chances of patient survival.

The methods of the present invention also contemplate the use of any number of arrangements and configurations of waveforms and waveshapes for the electrical stimulation pulse(s). Known monophasic, biphasic, triphasic and cross-phase stimulation pulses may be utilized. In one embodiment, the present invention contemplates the use of an ascending ramp waveform as described in the article Qu, F., Li, L., Nikolski, V. P., Sharma, V., Efimov, I. R., Mechanisms of Superiority of Ascending Ramp Waveforms: New Insights into Mechanisms of Shock-induced Vulnerability and Defibrillation, American Journal of Physiology-Heart and Circulatory Physiology, 2005, 289: H569-H577, the disclosure of which is incorporated herein by reference.

The methods of the present invention also contemplate the use of any number of arrangement and configurations for the generation of the phased unpinning far field electrical stimulation pulse(s). While conventional high voltage capacitor discharge circuitry may be utilized to generate the lower energy stimulation pulse(s) in accordance with the present invention, it is also expected that alternative arrangements could be utilized involving lower voltage capacitor arrangements, such as stacked, switched or secondary capacitors, rechargeable batteries, charge pump and voltage booster circuits as described, for example, in U.S. Pat. Nos. 5,199,429, 5,334,219, 5,365,391, 5,372,605, 5,383,907, 5,391,186, 5,405,363, 5,407,444, 5,413,591, 5,620,464 and 5,674,248, the disclosures of each of which are incorporated herein by reference. Generation of the staged/phased unpinning far field therapy in accordance with embodiments of the present invention can be accomplished by any number of methods, including known methods for generating pacing pulses. Similarly, any number of known techniques for cardiac arrhythmia detection may be used in accordance with the method of the present invention.

Three-Stage Atrial Cardioversion Therapy

Figure 10:
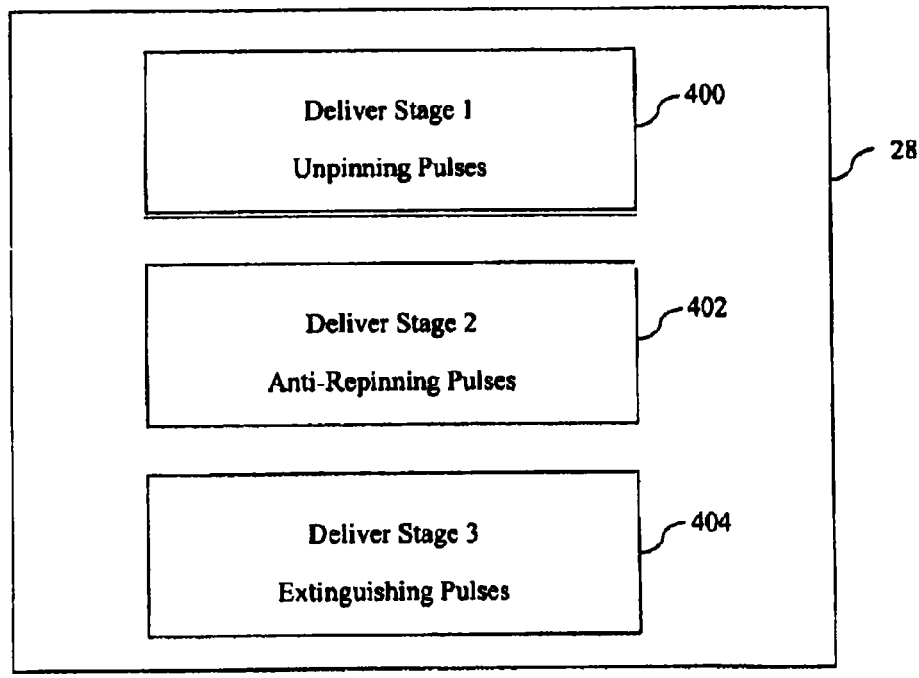
FIG. 10 depicts an embodiment of the FIG. 2 step of applying stimulation in the form of a three-stage cardioversion therapy.

In accordance with one embodiment the PUFFT therapy is delivered as part of a three-stage atrial cardioversion therapy. As shown in FIG. 10, in one embodiment the therapy (28) that is delivered by the method shown in FIG. 2 comprises a three-stage atrial cardioversion therapy delivered to the patient in response to detection of an atrial arrhythmia, the three-stage atrial cardioversion therapy having a set of therapy parameters and having a first stage (400) and a second stage (402) delivered via a far field configuration of the electrodes and a third stage (404) delivered via a near field configuration of the electrodes. It will be understood that "three stage" therapy refers to all variations of therapies of the claimed invention that include at least one set of first-stage pulses, at least one set of second-stage pulses, and at least one set of third-stage pulses. It will also be understood that "multi-therapy" includes multiple three-stage therapies, wherein the atrial arrhythmia may be reevaluated between three-stage therapy implementations.

Figure 11:
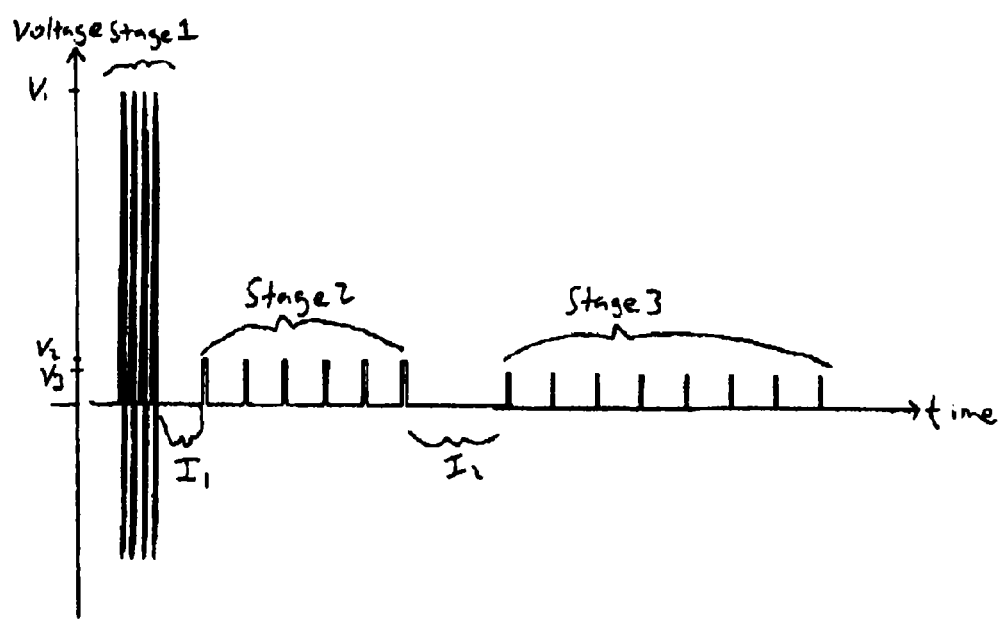
FIG. 11 depicts an embodiment of a stimulation waveform of the three-stage cardioversion therapy of FIG. 10.

Referring to FIG. 11, a combined representation of all three of the stages of the three-stage atrial cardioversion therapy is shown. A first stage (400) is applied for unpinning of one or more singularities associated with an atrial arrhythmia. A second stage (402) is applied for anti-repinning of the one or more singularities associated with the atrial arrhythmia. A third stage (404) is applied for extinguishing of the one or more singularities associated with the atrial arrhythmia.

In various embodiments, the first stage (400) has at least two and less than ten atrial cardioversion pulses of 10 volts to 100 volts. While depicted as biphasic, first stage (400) pulses may alternatively comprise monophasic or other custom-configured pulses. In an embodiment, the first stage (400) includes pulses ranging from 10 volts to 30 volts. Pulse duration may be approximately 3-4 milliseconds in some embodiments, or, more generally, of equals to or less than 10 milliseconds in various other embodiments, with a pulse coupling interval ranging from 20 to 50 milliseconds. In some embodiments, the first stage (402) has a total duration of less than two cycle lengths of the atrial arrhythmia.

In some such embodiments, the total duration may be determined as a percentage of the atrial fibrillation cycle length (AF CL), which in an embodiment ranges from 30 to 50% of a single AF CL. In other embodiments, the total duration of the first stage (402) may be greater than two cycle lengths of the atrial arrhythmia. The first stage may also generally be delivered within a ventricular refractory period. In an alternative embodiment, some first stage (402) pulses are delivered within the ventricular refractory period, and some without. In such an embodiment, individual or total pulse energy delivered within the ventricular refractory period may exceed the ventricular capture threshold in some cases, but those outside the ventricular refractory period would not, so as to avoid inducing ventricular fibrillation. In one embodiment, the energy of each biphasic atrial cardioversion pulse is less than 0.1 joules.

In an embodiment, an interstage delay (I1) of 50 to 400 milliseconds precedes the second stage (402), though in other embodiments, interstage delay I1 may be shorter or longer, such as 100 to 400 milliseconds.

In some embodiments, the second stage (402) has at least five and less than ten far field pulses of less than ventricular far-field excitation threshold (2 to 10 volts). Because second stage (402) is not directly synched to the R wave, pulse voltage and energy are generally kept low enough to minimize the risk of ventricular capture, though high enough to capture the atria. In an embodiment, pulse energy may be approximately equal to 1.5 times the energy needed to capture the atria. Though depicted as monophasic pulses, second stage (402) may comprise biphasic, monophasic or another non-traditional configuration, In an embodiment, second-stage pulse duration ranges from 5 ms to 20 milliseconds with a pulse coupling interval ranging from 70% to 100% of the cycle length of the atrial arrhythmia.

An interstage delay (I2) of between 50 to 400 milliseconds precedes the third stage (404), though in other embodiments, interstage delay I2 may be shorter or longer, such as 100 to 400 milliseconds.

In some embodiments, the third stage (404) has at least five and less than ten near field pulses, which may be biphasic, monophasic or of another non-traditional configuration, of less than 10 volts with a pulse duration of more than 0.2 and less than 5 milliseconds and a pulse coupling interval of 70 to 200% of the cycle length of the atrial arrhythmia. The three-stage atrial cardioversion therapy is delivered in response to detection of the atrial arrhythmia with each stage (400, 402 and 404) and in some embodiments, without confirmation of conversion of the atrial arrhythmia until after delivery of the third stage (404). Generally, as with second stage (402), enough energy should be applied so as to capture the heart with the pacing energy while still having enough energy margin to assure atrial capture.

Figure 12:
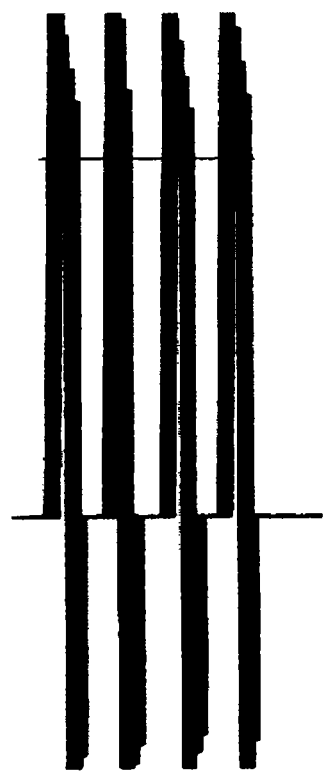
FIG. 12 depicts an embodiment of a first, unpinning stage of the waveform of FIG. 11.

Referring to FIG. 12, an embodiment of first stage (400) is shown. In this embodiment, each of four biphasic cardioversion pulses is delivered from a separate output capacitor arrangement where an H-bridge output switching arrangement reversals the polarity of the far-field electrodes at some point during the discharge of the output capacitor arrangement. In alternate embodiments, few output capacitor arrangements may be used where later cardioversion pulses are delivered from the same output capacitor arrangement that was used to delivery an earlier cardioversion pulse and that has been recharged before the later cardioversion pulse. In other embodiments, each phase of the biphasic cardioversion pulse may be delivered from a separate output capacitor arrangement. In other embodiments, a switching capacitor network may be used to combine output capacitor arrangements to deliver the cardioversion pulses of the first stage (400). It will be understood that the initial output voltage, reversal voltage, duration and coupling interval between pulses may be the same or different for all or for some of the pulses within the range of pulse parameters provided for the first stage (400). It will also be understood that the pulses shown in FIG. 12 of the first stage (400) may all be delivered through the same far-field electrode configuration, and in other embodiments the pulses may be delivered as part of a rotating set of PUFFT pulses delivered through different far-field electrode configurations.

Figure 13:
FIG. 13 depicts an embodiment of a second, anti-repinning stage of the waveform of FIG. 11.

Referring to FIG. 13, an embodiment of the second stage (402) is shown. In this embodiment, each of six monophasic far-field low voltage pulses are delivered from the same output capacitor arrangement that is recharged between successive pulses, although the pulses may each be delivered from separate output capacitor arrangements or from fewer output capacitor arrangements than the total number of pulses in the second stage (402). Alternatively, the pulses may be delivered directly from a charge pump, voltage booster or other similar kind of charge storage arrangement powered by a battery system. As with the first stage (400), it will be understood that the initial output voltage, duration and coupling interval between pulses of the second stage (402) may be the same or different for all or for some of the pulses within the range of pulse parameters provided for the second stage (402). It will also be understood that the pulses shown in FIG. 13 of the second stage (402) may all be delivered through the same far-field electrode configuration, and in other embodiments the pulses may be delivered as part of a rotating set of PUFFT pulses delivered through different far-field electrode configurations. The far-field electrode configuration for the second stage (402) may be the same as, or different than, the far-field electrode configuration utilized for the first stage (400).

Figure 14:
FIG. 14 depicts an embodiment of a third, extinguishing stage of the waveform of FIG. 11.

Referring to FIG. 14, an embodiment of the third stage (404) is shown. In this embodiment, each of eight monophasic near-field low voltage pulses are delivered from the same output capacitor arrangement that is recharged between successive pulses, although the pulses may each be delivered from separate output capacitor arrangements or from fewer output capacitor arrangements than the total number of pulses in the third stage (404). Alternatively, the pulses may be delivered directly from a charge pump, voltage booster or other similar kind of charge storage arrangement powered by a battery system. In one embodiment, the same output capacitor arrangement is used to deliver the second stage pulses and the third stage pulses. As with the first stage (400) and second stage (402), it will be understood that the initial output voltage, duration and coupling interval between pulses of the third stage (404) may be the same or different for all or for some of the pulses within the range of pulse parameters provided for the third stage (404). It will also be understood that the pulses shown in FIG. 14 of the third stage (404) may all be delivered through the same near-field electrode configuration, and in other embodiments the pulses may be delivered as part of a rotating set of PUFFT pulses delivered through different near-field electrode configurations. In some embodiments, the near-field electrode configuration may be a monopolar electrode arrangement, and in other embodiments, the near-field electrode configuration may be a bipolar electrode arrangement.

Figure 15:
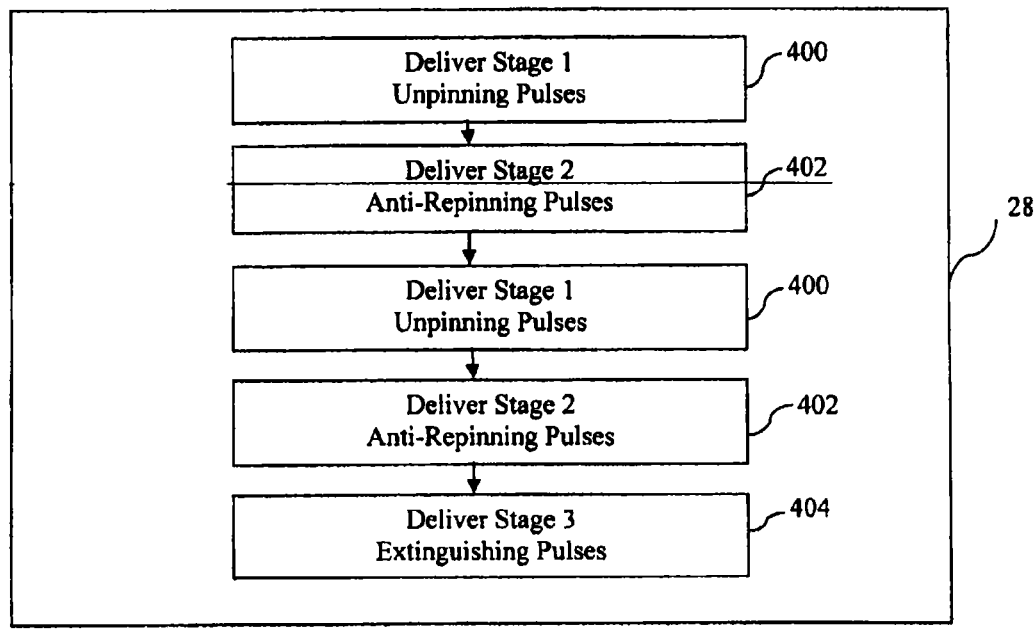
FIG. 15 depicts another embodiment of the FIG. 2 step of applying stimulation in the form of a three-stage cardioversion therapy.
Figure 16:
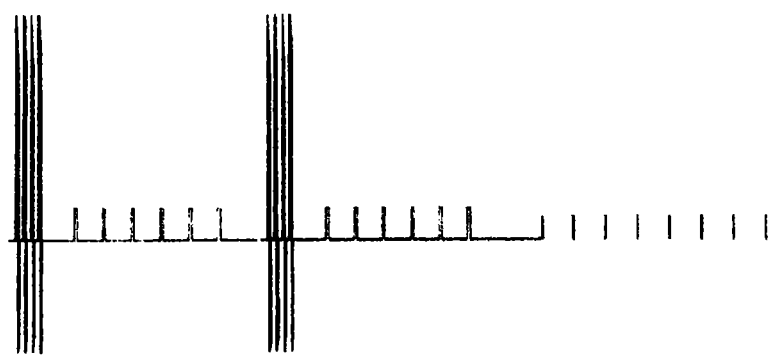
FIG. 16 depicts an embodiment of a stimulation waveform of the three-stage cardioversion therapy of FIG. 15.

Referring to FIGS. 15 and 16, a multi-therapy embodiment of the three-stage atrial cardioversion therapy is shown. In this embodiment, the unpinning stage 1 (400) and anti-repinning stage 2 (402) are each repeated in sequence as part of the overall atrial cardioversion multi-therapy before delivery of the extinguishing stage 3 (404). As with the embodiment shown in FIG. 11, the parameters for each of the stages, and each of the pulses within each stage, may be the same or different for different stages and/or different pulses within each stage. Generally, for multi-therapy, termination of the atrial arrhythmia may be confirmed between three-stage therapies, but not between individual stages (first, second, or third stages) of a three-stage therapy.

Figure 17:
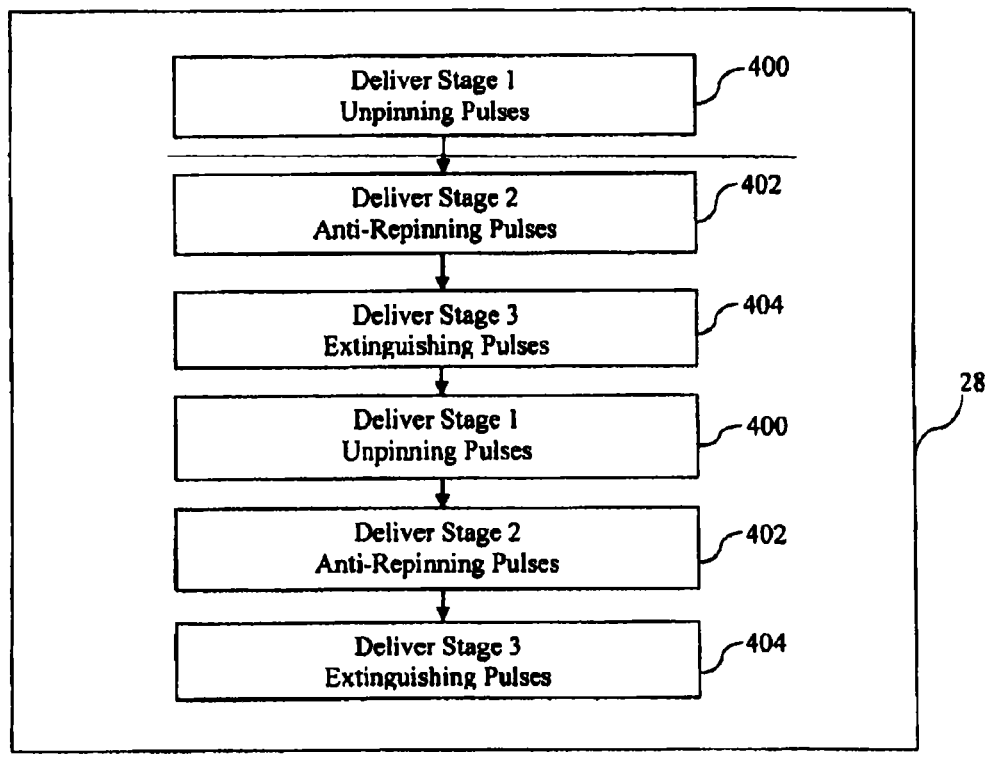
FIG. 17 depicts yet another embodiment of the FIG. 2 step of applying stimulation in the form of a three-stage cardioversion therapy.
Figure 18:
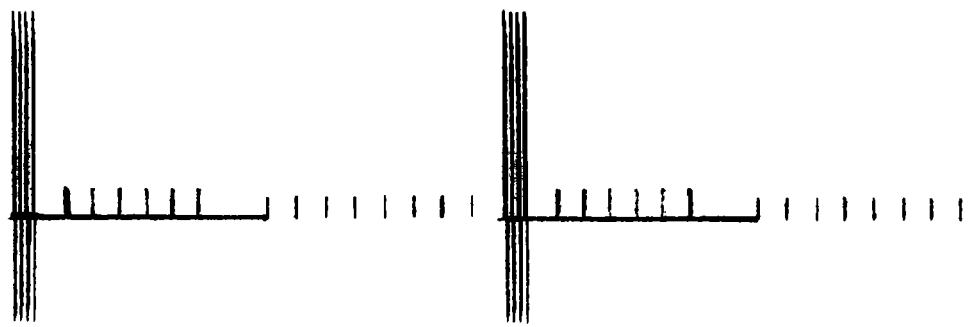
FIG. 18 depicts yet another embodiment of a stimulation waveform of the three-stage cardioversion therapy of FIG. 17.

Referring to FIGS. 17 and 18, an alternate embodiment of the three-stage atrial cardioversion therapy is shown. In this embodiment, the unpinning stage 1 (400) and anti-repinning stage 2 (402), as well as the extinguishing stage 3 (404) are each repeated in sequence as part of the overall atrial cardioversion therapy (28), followed by a repeated delivery of all three of the stages before completion of the atrial cardioversion therapy (28). As with the embodiment shown in FIG. 11, the parameters for each of the stages, and each of the pulses within each stage, may be the same or different for different stages and/or different pulses within each stage.

Figure 19A:
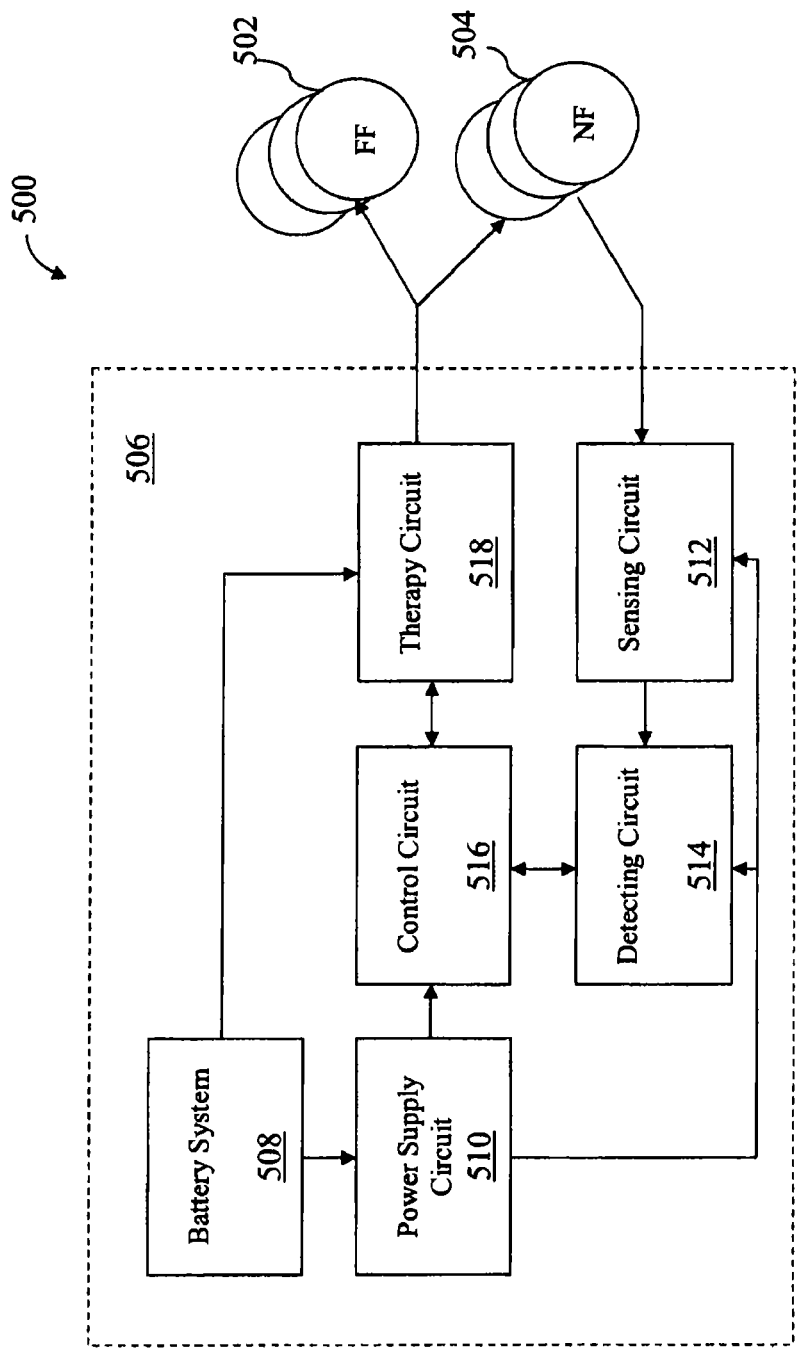
FIGS. 19A and 19B are block diagrams depicting of an embodiment of a three-stage cardioversion therapy device, and the therapy circuitry thereof, respectively.
Figure 19B:
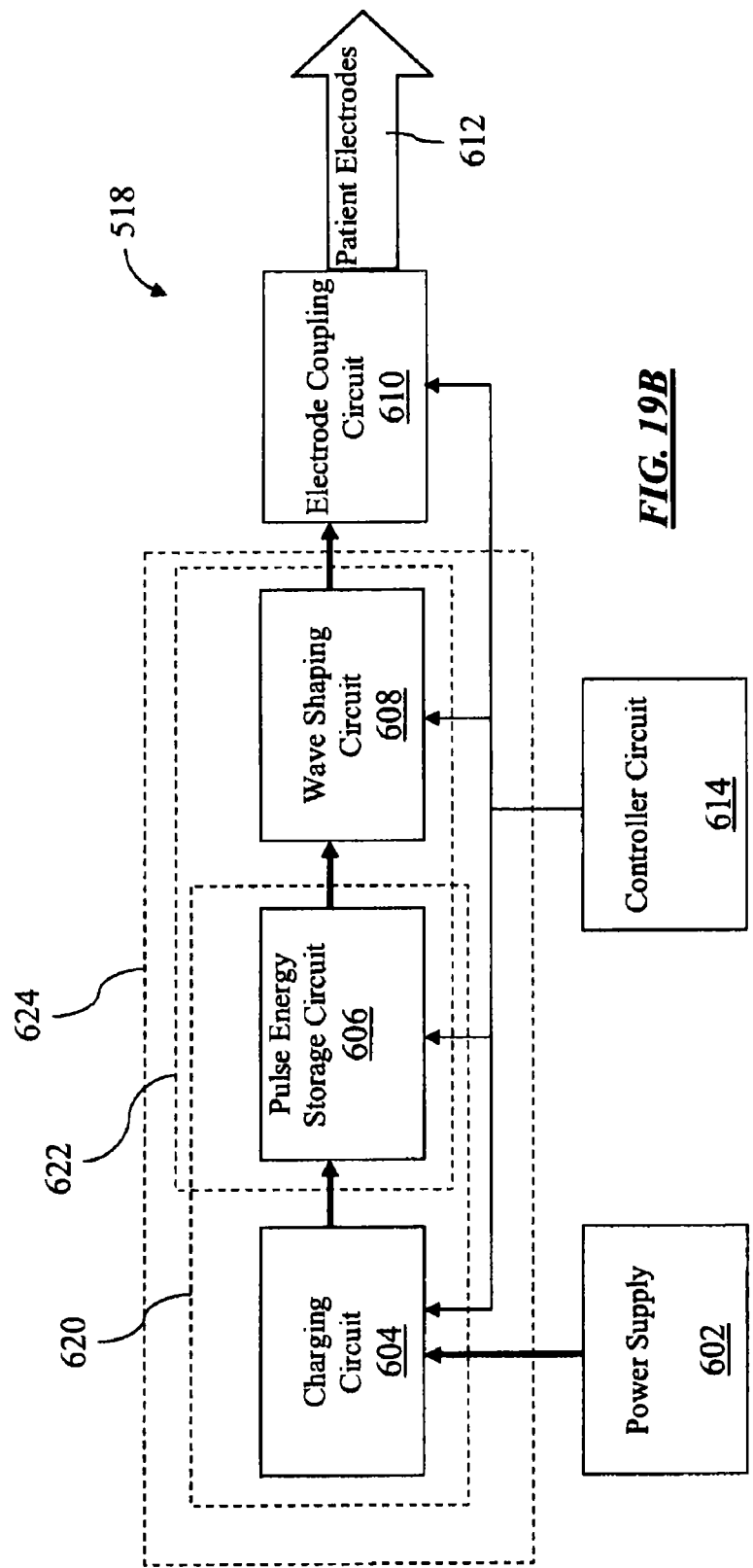

Referring now to FIGS. 19A-19B and 20, a detailed description of the construction of an embodiment of the three-stage atrial cardioversion system is described. In the example embodiment depicted in FIG. 19A at a high level, an atrial arrhythmia treatment apparatus 500 includes a plurality of electrodes 502 adapted to be implanted proximate an atrium of a heart of a patient to deliver far field pulses and a plurality of electrodes 504 adapted to implanted proximate the atrium of the heart of the patient to deliver near field pulses and sense cardiac signals. The housing of apparatus 500 can serve as one of the far-field electrodes 502 or near-field electrodes 504. Additionally, far-field electrodes 502 and near-field electrodes 504 can share at least one common electrode in some embodiments. An implantable therapy generator 506 is operably connected to the electrodes and includes a battery system 508 (or other suitable on-board energy source such as super capacitors, for example) and one or more power supply circuits 510 operably coupled and providing power to sensing circuitry 512, detection circuitry 514, control circuitry 516 and therapy circuitry 518 of the implantable therapy generator. In one type of embodiment, therapy circuitry 518 includes a specialized power supply that is fed directly from battery system 508, bypassing power supply circuitry 510. Sensing circuitry 512 senses cardiac signals representative of atrial activity and ventricular activity. Detection circuitry 514 evaluates the cardiac signals representative of atrial activity to determine an atrial cycle length and detect an atrial arrhythmia based at least in part on the atrial cycle length. Control circuitry 516, in response to the atrial arrhythmia, controls generation and selective delivery of a three-stage atrial cardioversion therapy to electrodes 502 and 504, with each stage having an inter-stage delay of between 100 and 400 milliseconds and, in an embodiment, without confirmation of conversion of the atrial arrhythmia during the three-stage atrial cardioversion therapy. In other embodiments, the inter-stage delay may be shortened, such that the inter-stage delay ranges from 50 to 400 milliseconds. In various embodiments, detection circuitry 514, control circuitry 516 and therapy circuitry 518 can share components. For example, in one embodiment, a common microcontroller can be a part of detection circuitry 514, control circuitry 516 and therapy circuitry 518.

The therapy circuitry 518 is operably connected to electrodes 502 and 504 and control circuitry 516. FIG. 19B illustrates an example arrangement of therapy circuitry 518 according to one type of embodiment. Therapy circuitry 518 can include its own power supply circuit 602, which is fed from battery system 508. Power supply circuit 602 can be a simple voltage regulator, or it can be a current limiting circuit that functions to prevent therapy circuitry (which has the greatest power demands of all the circuitry in the device) from drawing too much power and, consequently, causing a drop in the supply voltage below a sufficient level to power the controller and other critical components. Alternatively, power supply circuit 602 can be implemented in power supply circuit 510; or, in one type of embodiment, power supply circuit 602 can be omitted entirely, such that charging circuit 604 is fed directly from battery system 508.

Charging circuit 604 is a voltage converter circuit that produces voltages at the levels needed for the stimulation waveform. The input to charging circuit is a voltage at or near the voltage of battery system 508, which in one embodiment is between 3 and 12 volts. Since the stimulation waveform, particularly the first stage, is at a much higher voltage, up to around 100 volts, a boosting topology is used for charging circuit 604. Any suitable boosting circuit may be employed to this end, including a switching regulator utilizing one or more inductive elements (e.g., transformer, inductor, etc.), or a switching regulator utilizing capacitive elements (e.g., charge pump).

Figure 20A:
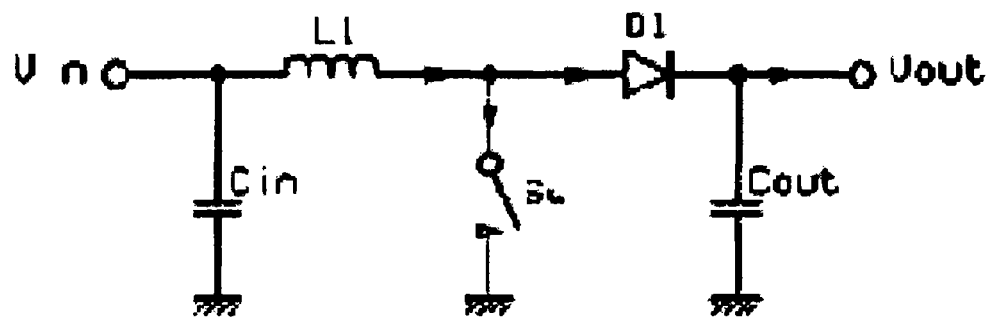
FIGS. 20A-20H depict various portions of the therapy circuitry of the device of FIGS. 19A and 19B, in greater detail, according to various embodiments.

FIGS. 20A-20F illustrate various known topologies for voltage boosting circuits that can be utilized as part of charging circuit 604 according to various embodiments. FIG. 20A illustrates a basic boost converter topology. The boost converter of FIG. 20A utilizes a single inductor indicated at L1 to store energy in each cycle of switch SW. When switch SW closes, inductor L1 is energized and develops a self-induced magnetic field. When switch SW opens, the voltage at the L1-SW-D1 node is boosted as the magnetic field in inductor L1 collapses. The associated current passes through blocking diode D1 and charges energy storage capacitor $C_{out}$ to a voltage greater than input voltage $V_{in}$.

Figure 20B:
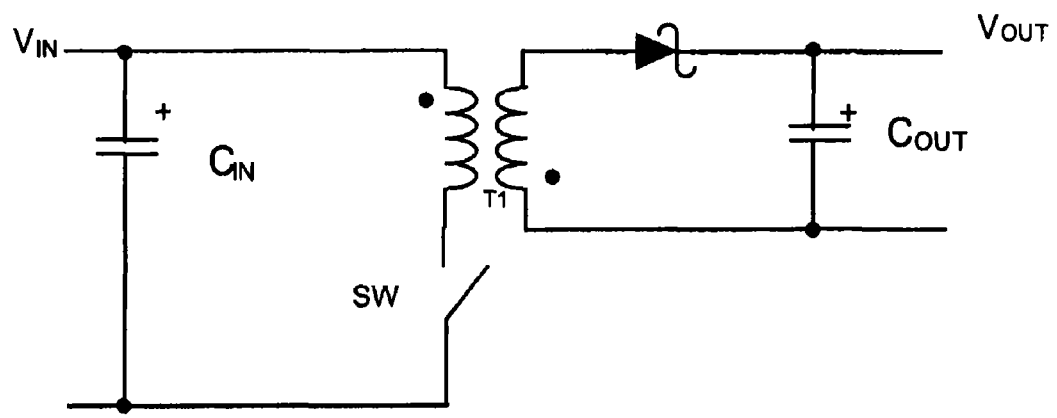

FIG. 20B illustrates a flyback converter topology. The flyback converter utilizes transformer T1 as an energy storage device as well as a step-up transformer. When switch SW is closed, the primary coil of transformer T1 is energized in similar fashion to inductor L1 of FIG. 20A. When switch SW opens, the voltage across the primary coil is reversed and boosted due to the collapsing magnetic field in the primary. The changing voltages of the primary coil are magnetically coupled to the secondary coil, which typically has a greater number of windings to further step-up the voltage on the secondary side. A typical turns ratio for defibrillator signal applications in certain embodiments is Np:Ns of about 1:15, where Np is the number of primary turns and Ns is the number of secondary turns. The high voltage across the secondary coil is rectified by the diode and stored in capacitor $C_{out}$.

Figure 20C:
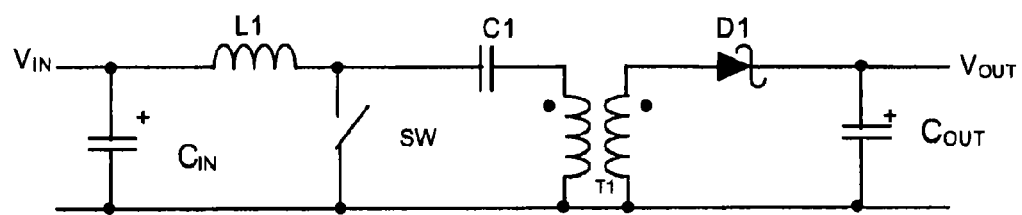

FIG. 20C illustrates a single ended primary inductance converter ("SEPIC"), which offers certain advantages over other power converter topologies. For instance, the SEPIC converter offers an advantage of not requiring significant energy storage in the transformer. Since most of the energy in a transformer is stored in its gap, this reduces the gap length requirement for the transformer. Battery voltage is applied at VIN and the switching element is switched at a fixed frequency and a duty cycle that is varied according to feedback of battery current into the power converter and output voltage. Voltage from the output of the step up transformer (T1) is rectified by the diode D1 to generate output voltage on $C_{out}$.

Figure 20D:
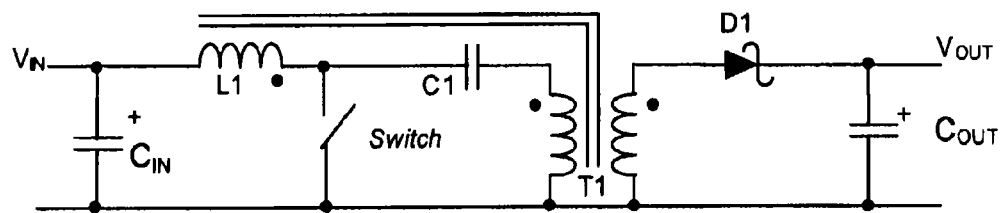

FIG. 20D illustrates a variation of the SEPIC converter of FIG. 20C. The SEPIC topology of FIG. 20D has an additional inductive component (L1). The additional inductor L1 can be implemented either discretely, or can be magnetically coupled with the high voltage transformer into a single magnetic structure, as depicted in FIG. 20D.

Figure 20E:
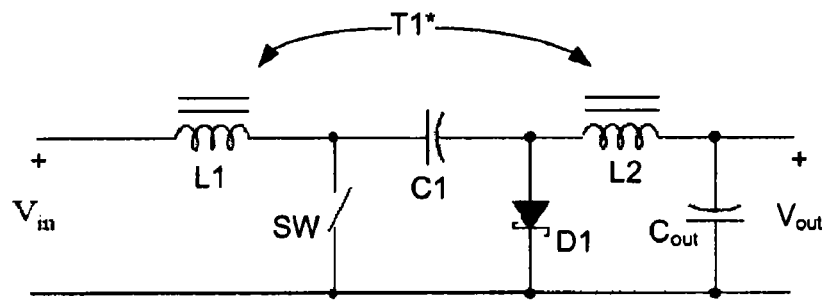

FIG. 20E illustrates a Cuk converter topology. A Cuk converter comprises two inductors, L1 and L2, two capacitors, C1 and $C_{out}$, switch SW, and diode D1. Capacitor C is used to transfer energy and is connected alternately to the input and to the output of the converter via the commutation of the transistor and the diode. The two inductors L1 and L2 are used to convert, respectively, the input voltage source ($V_i$) and the output voltage at capacitor $C_{out}$ into current sources. Similarly to the voltage converter circuits described above, the ratio of output voltage to input voltage is related to the duty cycling of switch SW. Optionally, inductors L1 and L2 can be magnetically coupled as indicated T1*.

Figure 20F:
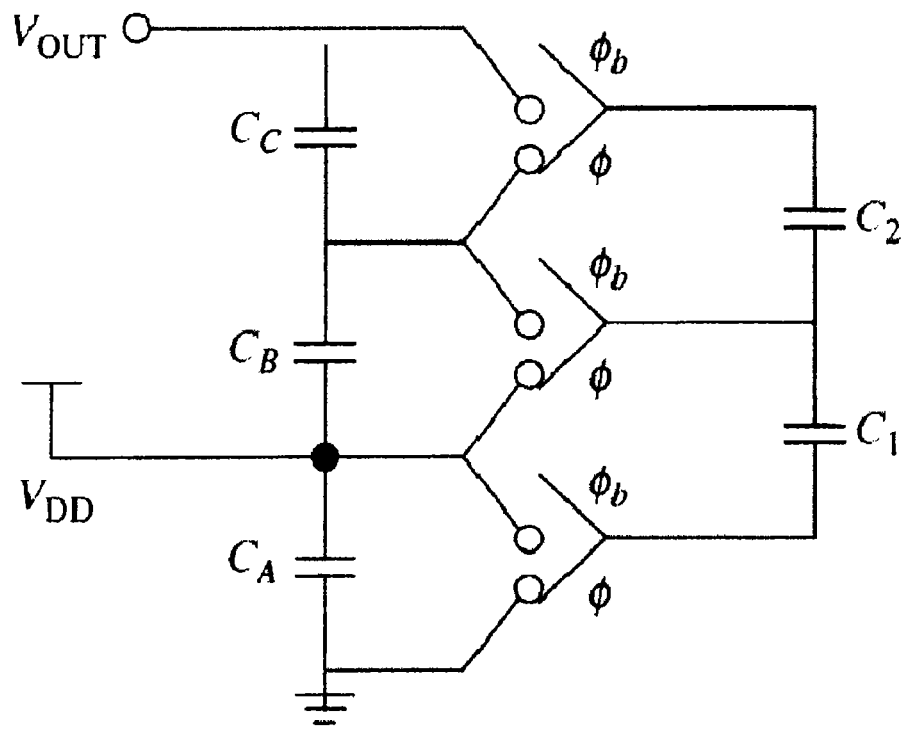

FIG. 20F illustrates a basic charge pump topology for multiplying the input voltage. The example shown is a Cockcroft-Walton multiplying circuit. Three capacitors ($C_A$, $C_B$, and $C_C$), each of capacity C, are connected in series, and capacitor $C_A$ is connected to the supply voltage, $V_{DD}$. During phase $\phi$, capacitor $C_1$ is connected to $C_A$ and charged to voltage $V_{DD}$.

When the switches change position during the next cycle, $\phi_b$, capacitor $C_1$ will share its charge with capacitor $C_B$, and both will be charged to $V_{DD}/2$ if they have equal capacity. In the next cycle, $C_2$ and $C_B$ will be connected and share a potential of $V_{DD}/4$, while $C_1$ is once again charged to $V_{DD}$. As this process continues for a few cycles, charge will be transferred to all the capacitors until a potential of $3V_{DD}$ is developed across the output Vout. Additional stages may be added to increase the voltage multiplication.

Figure 20G:
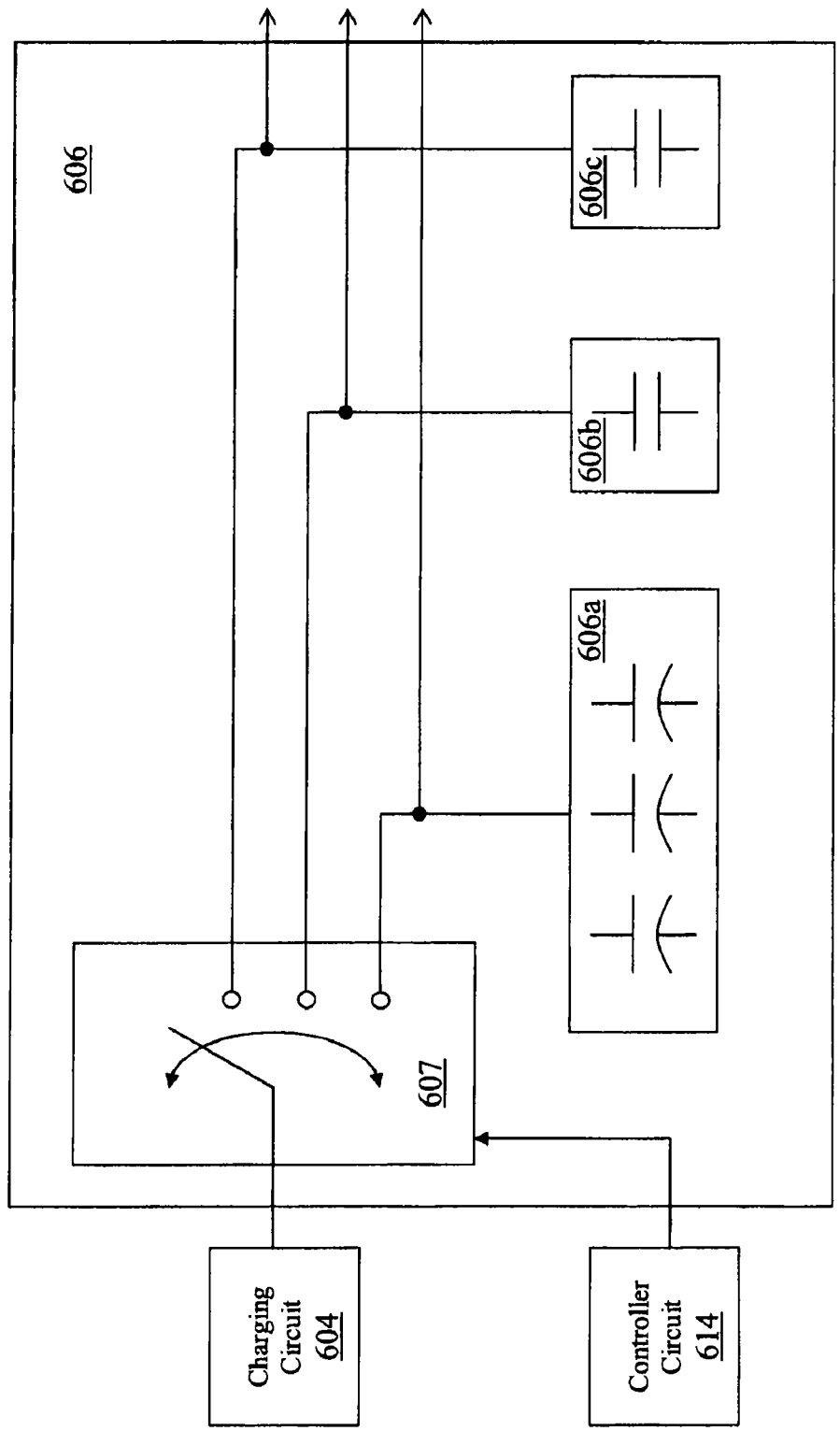
Figure 20H:
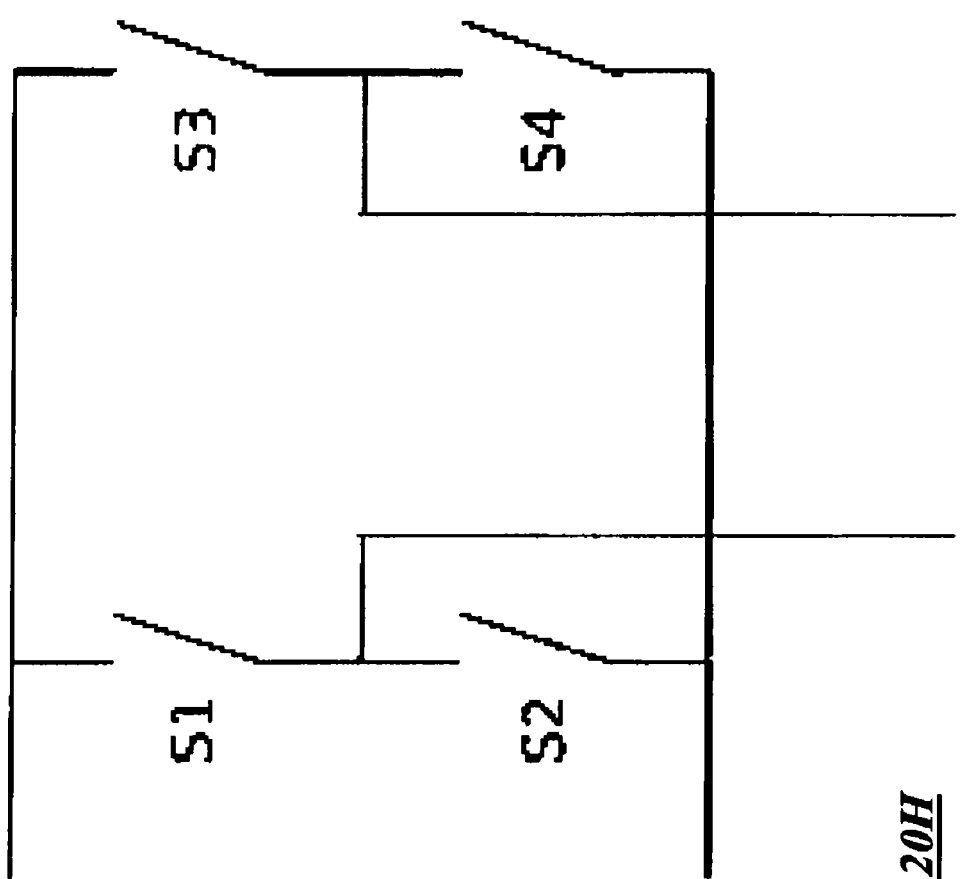

Referring again to FIG. 19B, pulse energy storage circuit 606 can take various forms. Generally, pulse energy storage circuit has energy storage capacity sufficient to store either all three stages of the atrial cardioversion therapy, or a portion of the therapy's energy, provided that the arrangement of energy storage circuit 606 and charging circuit 604 supports the ability to re-charge portions of the energy storage circuit 606 while other portions thereof are discharging or are about to discharge during application of the electrotherapy. FIG. 20G illustrates a basic example of energy storage circuit 606, in which there are three separate storage reservoirs for each of the three stages of the electrotherapy. Storage reservoir 606a stores the energy for the first stage; storage reservoir 606b for the second; and 606c for the third. Each storage reservoir can have one, or a plurality of storage elements. In one type of embodiment, each storage reservoir has a plurality of storage element groups, with each storage element group individually switchably selectable for charging and discharging. The storage elements can take any suitable form, including capacitors of a suitable technology, e.g., electrolytic, tantalum film, ceramic chip, supercap, or the like.

Storage reservoirs 606a-606c are coupled to charging circuit 604 via selector switch 607. Selector switch 607 can be implemented with a analog multiplexer, transmission gates, or any other suitable electronic switching arrangement. Selector switch 607 is controlled by controller circuit 614 in this example.

Referring again to FIG. 19B, wave shaping circuit 608 regulates the application of the electrotherapy by selecting, and controlling the discharging of the energy stored in energy storage circuit 606. In one embodiment, wave shaping circuit 608 is in the form of a H-bridge topology, as illustrated in FIG. 20G. Switches S1-S4 are individually controlled by controller circuit 614. The H-bridge topology facilitates steering, or reversing the polarity, of the electrotherapy signals, enabling a biphasic shock to be applied from a single-polarity energy storage reservoir. Other forms of switchable coupling are also contemplated for other embodiments. For instance, a set of analog transmission gates can be used, such that each storage reservoir 606a-606c is individually selectable. In this latter example, separate capacitors of opposite polarity are used for storing the charge for each phase of the biphasic unpinning waveform of the first electrotherapy phase.

Referring again to FIG. 19B, electrode coupling circuit 610 operates to select which of the multiple sets of patient electrodes 612 are coupled to the output of the wave shaping circuit 608. Electrode coupling circuit 610 can be implemented in one example embodiment using a set of analog multiplexers that are controlled by controller circuit 614.

In various other embodiments, the functionality of charging circuit 604 and pulse energy storage circuit 606 can be combined into a single circuit 620, such as a charge pump arrangement, in which certain ones of the capacitors are also used for both, building up charge, and storing the pulse energy for the electrotherapy. In another variation, the pulse energy storage circuit 606 can be one and the same circuit, as the wave shaping circuit 608, depicted at 622, such as, for example, where multiple different capacitors are used to store each individual pulse, and where the electrode coupling circuit has the capability to individually select which capacitors are switched in to which electrodes. Moreover, in yet another variation, charging circuit 604, pulse energy storage circuit 606, and wave shaping circuit 608 can be combined as a single circuit implementation 624, which can be implemented as a combination of circuits 620 and 622.

Figure 21:
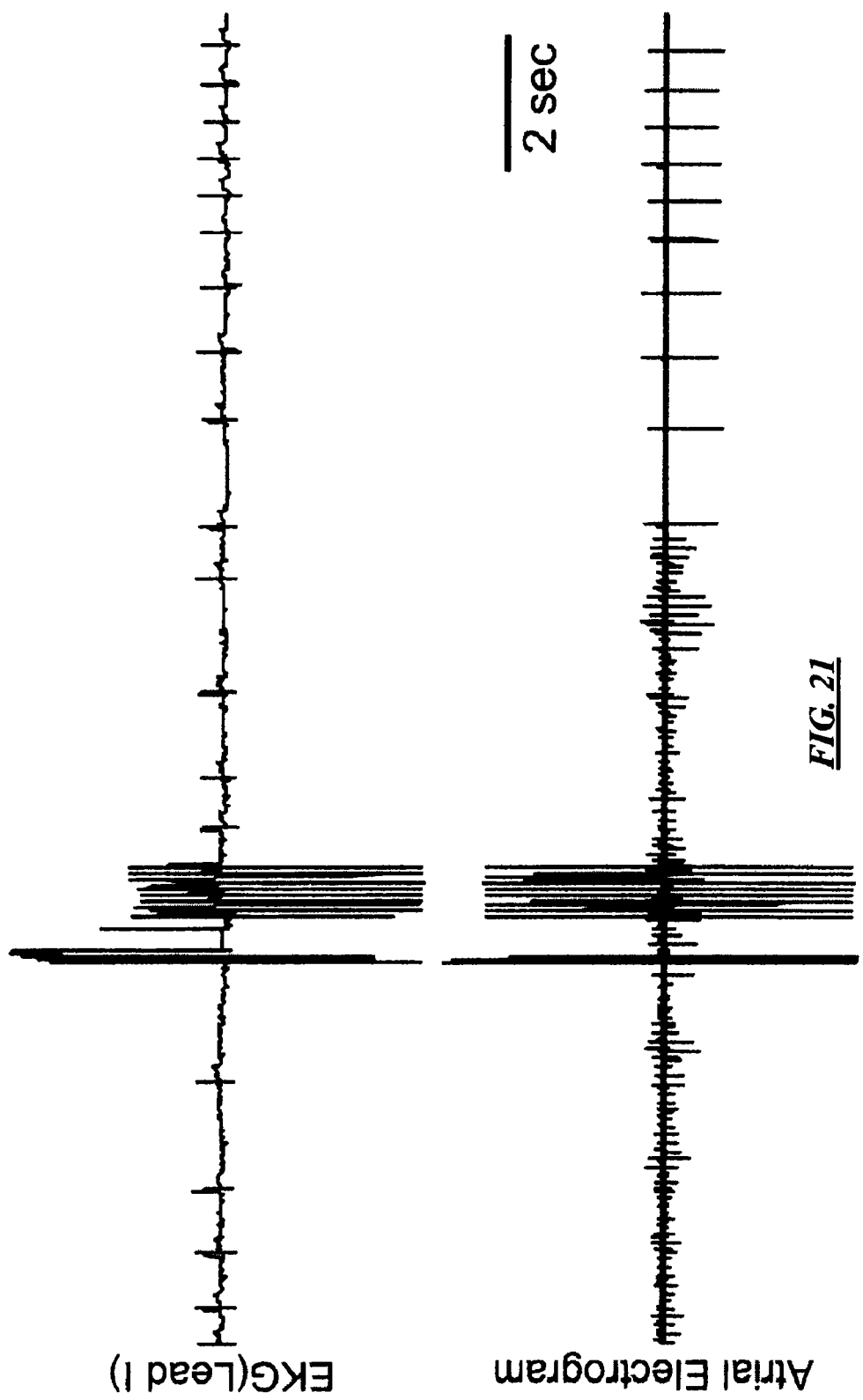
FIG. 21 depicts an EKG waveform of a canine subject receiving the three-stage cardioversion therapy of FIG. 10.
Figure 22:
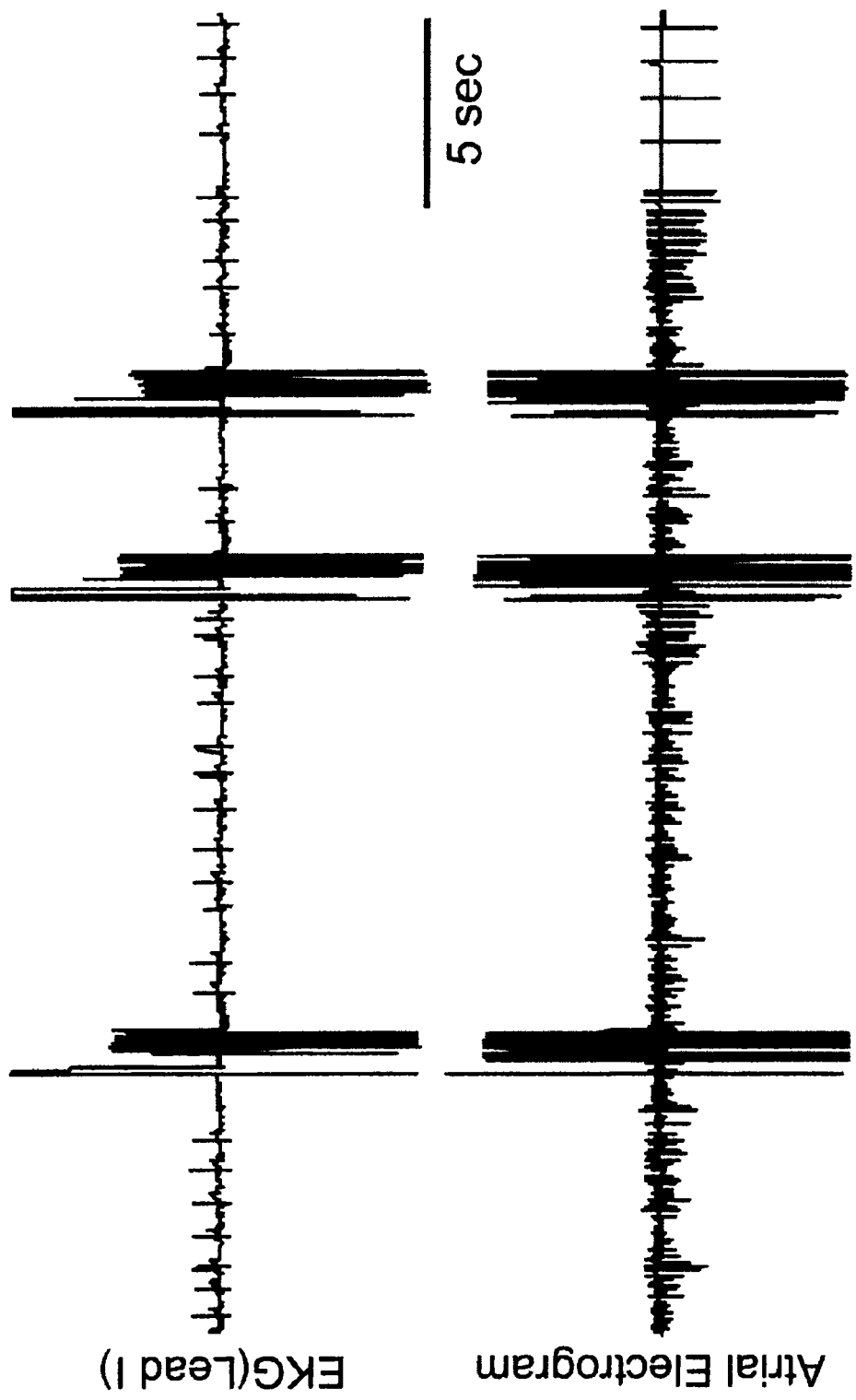
FIG. 22 depicts an EKG waveform of a canine subject receiving the three-stage cardioversion therapy of FIG. 16.

Referring now to FIGS. 21 and 22, exemplary EKG outputs are shown with the three-stage atrial cardioversion therapy overlayed to demonstrate how the three-stage atrial cardioversion therapy successfully converts an atrial arrhythmia. FIG. 21 illustrates two curves, the top curve showing the signal measured with the EKG lead; and the top curve showing the signal measured with another lead in the atrium. The electrotherapy is applied from the RAA to the LAA. As shown, in the first stage, two unpinning biphasic shocks at 30V with an interval of 40 ms are applied. Then, in the second stage, eight anti-repinning monophasic shocks at 3V are applied with an interval of 100 ms using the same electrodes as those in the first stage. Subsequently, in the third stage, eight pacing stimuli are applied with an interval of 100 ms. The third stage is applied via a RA epicardial pacing electrode. As shown in the lower curve, the atrial fibrillation is restored to a normal sinus rhythm following administration of the therapy. FIG. 22 depicts a similar pair of curves, except that the three-stage electrotherapy is applied in three trials. In the first trial, the first stage applied has five unpinning biphasic shocks at 20V with an interval of 20 ms. In the second stage of the first trial, eight anti-repinning monophasic shocks at 3V with an interval of 100 ms are applied from the same electrodes as the first stage. In the third stage of the first trial, eight pacing stimuli with an interval of 100 ms are applied from the RA epicardial pacing electrode.

The second and third trials of the three-stage therapy are applied in similar fashion, except that in the first stage of trials 2 and 3, five unpinning biphasic shocks are applied at 30V with an interval of 20 ms. As can be seen in the lower curve of FIG. 22, the atrial EKG indicates restoration of a normal sinus rhythm following administration of the three trials.

Figure 23:
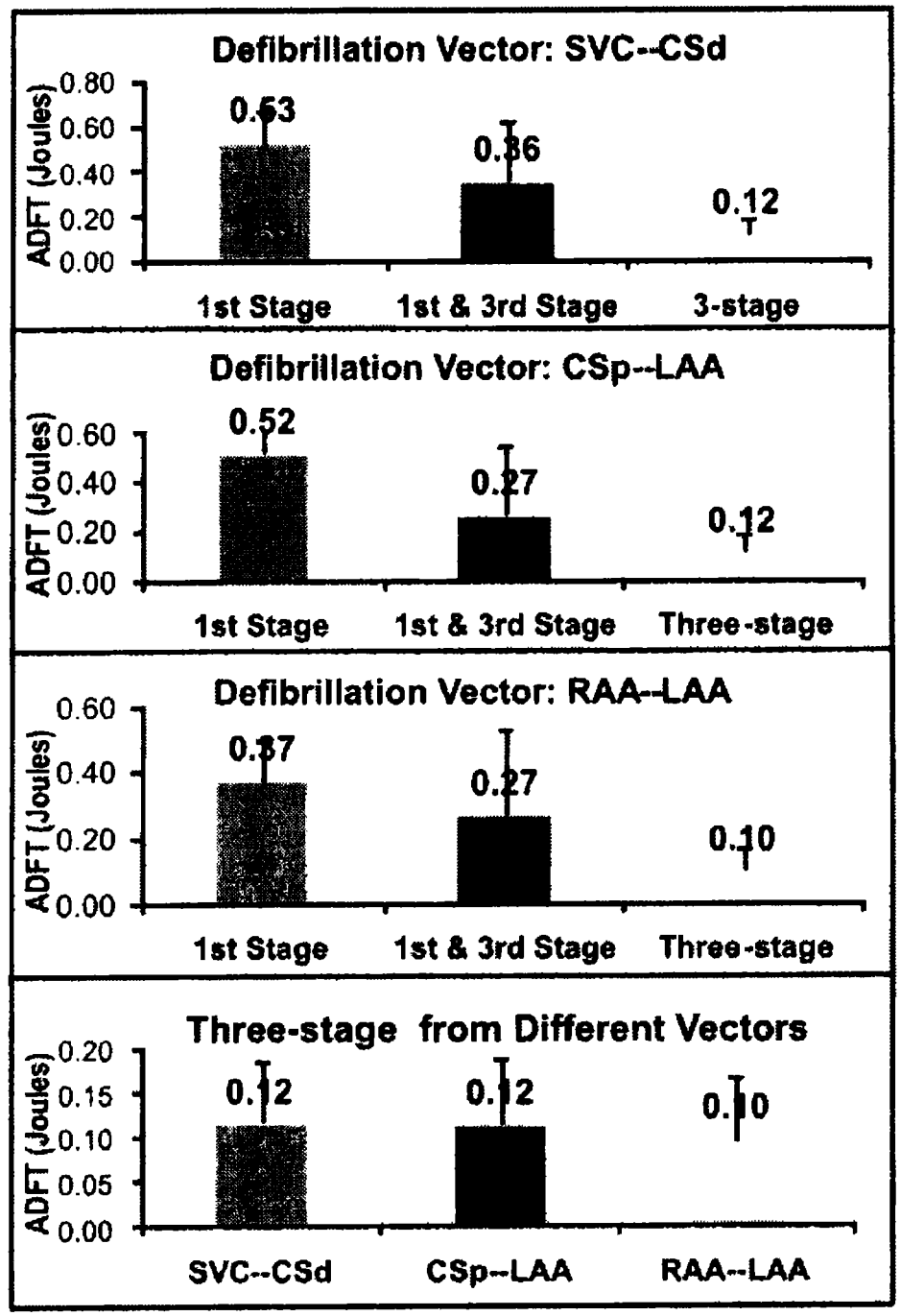
FIG. 23 depicts four bar charts summarizing the energy applied during various applications of one-, two-, and three-stage therapy across three different vectors.

Referring now to FIG. 23, experimental results of a comparison of the results in terms of energy required for successful conversion of AF for three different electrode configuration vectors is shown for a shock only protocol, a shock followed by ATP and for the three-stage atrial cardioversion therapy in accordance with an embodiment of the present invention.

In the first part of the study, eight mongrel dogs were used. Two disk electrodes with a diameter of 1" were placed on the right atria (RAA) and the left atria appendage (LAA), respectively. AF was induced by the rapid atrial pacing in the presence of stimulating bilateral vagus nerve at frequency of 4~20 Hz. AF that lasted for >5 min was defined as sustained AF. 1 to 4 monophasic (MP, 10 ms) or biphasic (BP, 6-4 ms) shocks were applied from disk electrodes, followed with or w/o ATP applied from an atrial epicardium-pacing electrode. All shocks are triggered by the right ventricular R-wave and applied within 80~100 ms to avoid VF induction. In six dogs, a mainly sustained AF was observed with dominant frequency of $11.0 \pm 1.7$ Hz using vagal stimulation at $12.0 \pm 4.4$ Hz. For AF (95% cases), DFT of 1BP was lower than that of 1MP ($0.73 \pm 0.43$ vs. $1.68 \pm 0.98$ J, p=0.008). DFT of 2BP was lower than that of 2MP ($0.37 \pm 0.14$ vs. $0.93 \pm 0.59$ J, p=0.01). DFT of 2BP was lower than that of 1BP ($0.37 \pm 0.14$ vs. $0.73 \pm 0.43$ J, p=0.04). There are no significant difference among DFTs of 2BP, 3BP, and 4BP, while DFT of 4BP is higher than that of 3BP ($0.53 \pm 0.41$ vs. $0.39 \pm 0.36$ J, ns). 2BP followed by 6 pulses of ATP lower the DFT significantly than that of 2BP ($0.23 \pm 0.05$ vs. $0.5 \pm 0.08$ J, p=0.001). Atrial flutter (5% cases, which had dominant frequency of $7.7 \pm 0.4$ Hz) can easily be converted by multiple shocks at $0.0003 \pm 0.0001$ J. or ATP alone.

In the second part of the study, eight mongrel dogs were used. Three disk electrodes with a diameter of 0.5" were placed on the RAA, LAA, and superior vena cava (SVC). A 3F lead with two 1" coils was inserted into coronary sinus. The distal coil is named as coronary sinus distal (CSd) and the proximal coil is named as coronary sinus proximal (CSp). We tested DFT of shocks applied from three vectors: SVC to CSd, LAA to CSp, and LAA to RAA. Three different combinations of the three stages were tested randomly: 1st stage only, 1st stage followed by 2nd stage, and three stages together, named as therapy 1, therapy 2, and therapy 3, respectively. In six out of eight dogs, sustained AF with dominant frequency of $9.77 \pm 0.88$ Hz was induced. In all three vectors, the therapy 3 had the lowest DFT among three therapies. The therapy 1 had the highest DFT among three therapies. In vector SVC to CSd, DFTs of therapy 1, therapy 2, and therapy 3 were $0.53 \pm 0.14$ vs. $0.35 \pm 0.26$ vs. $0.12 \pm 0.070$ J. In vector LAA to CSp, DFTs of therapy 1, therapy 2, and therapy 3 were $0.52 \pm 0.14$ vs. $0.27 \pm 0.27$ vs. $0.12 \pm 0.074$ J. In vector RAA to LAA, DFTs of therapy 1, therapy 2, and therapy 3 were $0.37 \pm 0.13$ vs. $0.27 \pm 0.26$ vs. $0.097 \pm 0.070$ J. There is not significant difference among DFTs of three vectors.

Additional details of the above-described study may be found in the published article to Li et al., Low Energy Multi-Stage Atrial Defibrillation Therapy Terminates Atrial Fibrillation with Less Energy than a Single Shock, Circulation Arrhythmia and Electrophysiology, published online Oct. 6, 2011, which is hereby incorporated by reference in its entirety.

Figure 24:
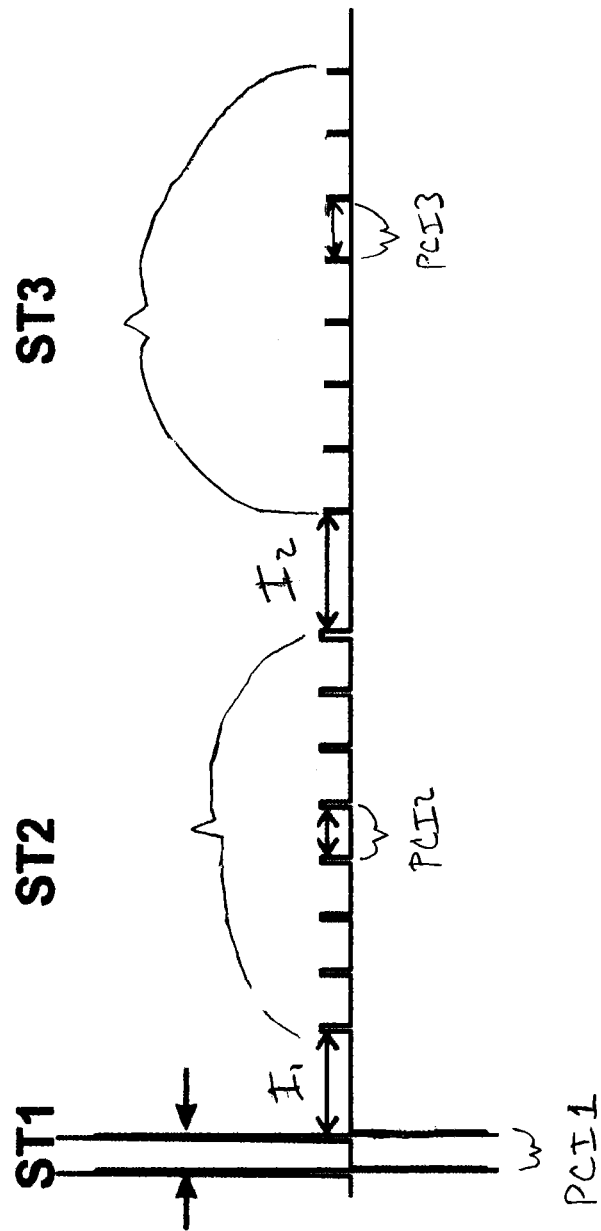
FIG. 24 depicts another embodiment of a three-stage therapy as implemented in a canine model.

Referring now to FIG. 24, an embodiment of the three-stage therapy of FIG. 11 that was experimentally shown to successfully defibrillate/cardiovert AF at low energy is depicted. As will be described further below with respect to FIGS. 29 and 30, this particular three-stage therapy was applied using an implantable device in a chronic canine model of persistent AF.

In this tested embodiment, first stage (ST1) consisted of two low-energy bi-phasic pulses having peak voltages ranging from 10 volts to 100 volts. Pulse duration ranged from 4-10 ms, with a pulse-coupling interval (PCI1) ranging from 30 to 50% of the AF CL. The pulses were synchronized to the R wave and delivered within the ventricular effective refractory period to avoid inducing ventricular fibrillation.

After delivering first stage (ST1) pulses, an inter-stage delay (I1) of 50 ms to 400 ms was implemented. More particularly, the interstage delay (I1) was 50 ms, followed by second stage (ST2).

Second stage (ST2) consisted of six ultra-low-energy monophasic pulses. Peak voltages ranged from 1 volt to 3 volts, each having an approximate pulse duration of 10 ms. Pulses were delivered at 70% to 100% of the AF CL (pulse-coupling interval PCI2). In at least one case, pulses were delivered at 88% of the AF CL. In this stage, the multiple pulses delivered enough energy to capture the atrium, but not the ventricle. Operating in this voltage window above the atrial capture threshold, but below the ventricular capture threshold is necessary because the second stage (ST2) pulses are delivered at 70% to 100% of the AF CL, and not synchronized to the R wave. If second stage (ST2) voltage or energy becomes too high, there exists a risk of capturing the ventricle and inducing ventricular fibrillation.

After delivering second stage (ST2) pulses, an inter-stage delay of 50 ms to 400 ms was implemented. More particularly, the inter-stage delay was 50 ms, followed by third stage (ST3).

Third stage (ST3) consisted of pacing the atrium generally at 70% to 100% of the AF CL (PCI3 of 70% to 100% of AFCL), but more particularly at 88% of the AF CL, at three times the atrial capture threshold.

Referring also to FIGS. 25A-25D, a chronic canine model of persistent AF through chronic high-rate atrial pacing was created to implement the three-stage therapy of FIG. 24.

In this study, a transvenous endocardial lead system was implanted to deliver the sequential, three-stage therapy of FIG. 24 in a closed-chest canine model of persistent AF induced by rapid atrial pacing. Bipolar pace/shock leads were implanted in the right atrium (RA) and left pulmonary artery (LPA), reproducing an RA to distal coronary sinus vector. Persistent AF was induced by high-rate atrial pacing for 8-12 weeks. The atrial DFTs of three-stage therapy and a single biphasic shock were delivered through the RA-LPA vector and measured.

The three-stage therapy, as depicted and described above with respect to FIG. 24, consisted of three sequential stages: two biphasic shocks (pulses) delivered within one AF cycle length as well as ventricular effective refractory period; six monophasic pulses, each delivered with an interval of 88% of the AF CL at 50% of the ventricular capture voltage; and anti-tachycardia pacing (ATP; 8 pulses with an interval 88% of the AF CL) delivered through the RA bipole.

Referring specifically to FIGS. 25A-25D, lead placement of the canine model is depicted. Bipolar pacing/sensing lead 500 was implanted in the right atrial appendage (RAA) and SVC as depicted. Lead 502 with electrode 504 was implanted in the CS as depicted. Lead 506 with proximal and distal electrodes 508a and 508b was implanted in the LPA as depicted. An LPA lead was chosen due to the anatomical differences between the canine and human coronary sinus. The CS of a dog tapers quickly, preventing insertion of leads into the lateral CS, so an LPA-implanted lead was used to approximate the lateral CS of a human.

Atrial tachypacing pulses were delivered from an implantable device, including a Medtronic Entrust implantable cardioverter defibrillator manufactured by Medtronic of Minneapolis, Minn.

The above-described implantable, closed-chest model was selected recognizing that previous work was done in an acute vagus nerve stimulated AF canine model, which is much different than humans with AF. Secondly, previous studies often used defibrillation disks in an open-chest model, which is generally not a realistic approach for humans.

Results indicated a mean dominant frequency of AF of 114±17 ms. The impedance of the RA-LPA vector was 103.1±15.7 Ohms. As depicted, three-stage therapy significantly decreased the atrial DFT compared to a single biphasic shock with respect to total energy (0.27±0.14 J versus 1.45±0.36 J; $p<0.001$) and peak voltage (42.3±14.8 V versus 161.2±18.7 V, $p<0.001$).

During the study, fourteen dogs were implanted; AF was induced in ten of the dogs, with an average time between implantation and AF induction being six weeks +/− two weeks. Twenty-two defibrillation studies were performed in six dogs, and 127 terminations of AF completed with the average AF CL and mean impedance described above.

Figure 26:
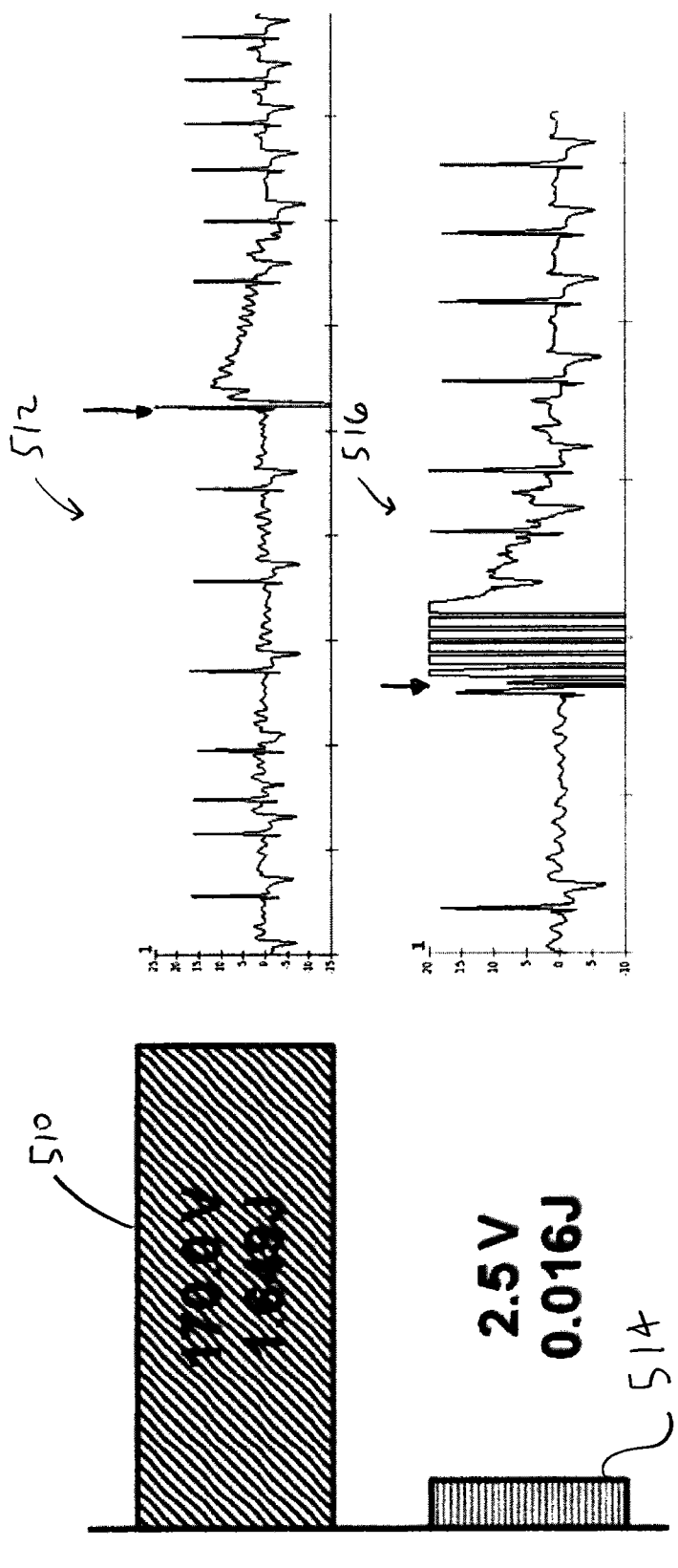
FIG. 26 depicts a sample comparison of atrial DFTs and corresponding electro-cardiograms of a single-biphasic shock and the three-stage therapy of FIG. 24.
Figure 27:
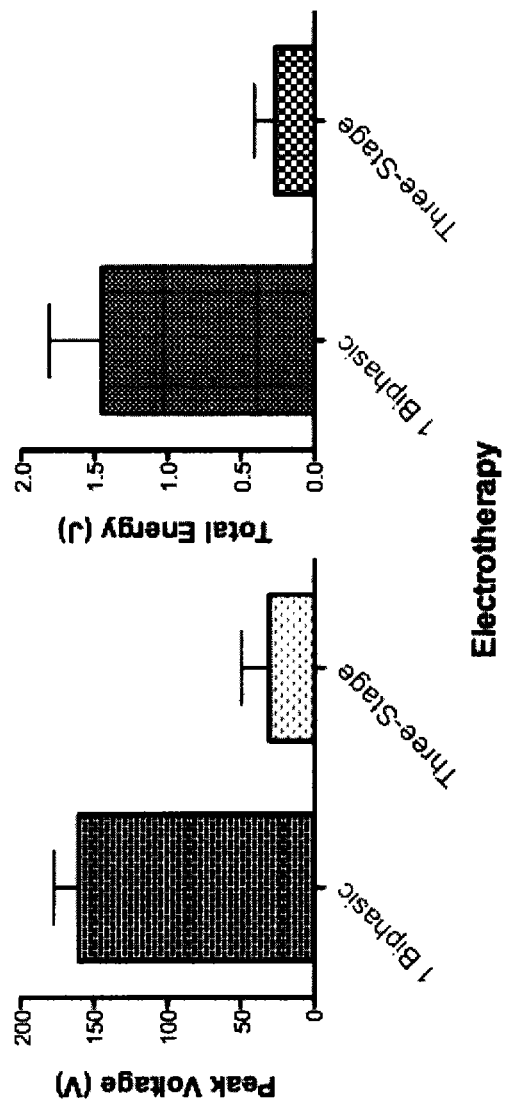
FIG. 27 depicts another sample comparison of atrial DFTs of a single-biphasic shock and the three-stage therapy of FIG. 24.

Referring to FIGS. 26-27, sample atrial DFTs resulting from the three-stage therapy of the claimed invention were significantly lower than those of a conventional biphasic shock therapy.

Referring specifically to FIG. 26, a bar chart depicts an overall voltage and energy comparison of atrial DFTs of a single biphasic shock and the three-stage therapy of the claimed invention. Also depicted are the corresponding sample ECGs.

Bar 510 depicts the voltage and energy characteristics of an atrial DFT corresponding to a single, biphasic shock. ECG 512 depicts the ECG of the atrial arrhythmia interrupted by the biphasic shock as indicated by the arrow. As depicted, the DFT voltage was 170.0 volts at a total energy of 1.649 Joules.

Bar 514 depicts the voltage and energy characteristics of an atrial DFT corresponding to the three-stage therapy of the claimed invention as described above. ECG 516 depicts the ECG of the atrial arrhythmia interrupted by the three-stage therapy at a timing indicated by the arrow. As depicted, the DFT voltage was 2.5 volts at a total energy of 0.016 Joules.

As such, the AF was terminated by the three-stage therapy with significantly less energy and lower peak voltage as compared to the single biphasic shock.

Referring to FIG. 27, in another example, AF was terminated with less energy and lower peak voltage using the three-stage therapy of the claimed invention as compared to a single biphasic shock.

Peak voltage was reduced to 42.3±14.8 V versus 161.2±18.7 V for a single BP shock ($p<0.001$).

Atrial DFT was reduced to 0.27±0.14 J versus 1.45±0.36 J for a single BP shock ($p<0.001$).

Consequently, the three-stage electrotherapy of the present invention terminates persistent AF with significantly lower peak voltage and dramatically lower total energy compared to a conventional single biphasic shock. Further, this therapy may enable device-based painless atrial defibrillation by defibrillating at thresholds below the human pain threshold.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A three-stage atrial arrhythmia treatment apparatus, comprising:

at least one electrode adapted to be implanted proximate an atrium of a heart of a patient to deliver far field pulses;

at least one electrode adapted to implanted proximate the atrium of the heart of the patient to deliver near field pulses and sense cardiac signals;

an implantable therapy generator adapted to be implanted in a patient and operably connected to the electrodes, including:

sensing circuitry that senses cardiac signals representative of atrial activity and ventricular activity;

detection circuitry operably connected to the sensing circuitry to evaluate the cardiac signals representative of atrial activity to determine an atrial cycle length and detect an atrial arrhythmia based at least in part on the atrial cycle length;

control circuitry operably connected to the sensing circuitry that, in response to the atrial arrhythmia, controls generation and selective delivery of a three-stage atrial cardioversion therapy to the electrodes with each stage having an inter-stage delay of between 50 to 400 milliseconds and without confirmation of conversion of the atrial arrhythmia during the three-stage atrial cardioversion therapy; and therapy circuitry operably connected to the electrodes and the control circuitry including:

at least one first stage charge storage circuit selectively coupled to the at least one far field electrode that selectively stores energy for a first stage of the three-stage atrial cardioversion therapy having at least two and less than ten atrial cardioversion pulses of at least 10 volts and not more than 100 volts, wherein the first stage has a total duration of less than one cycle lengths of the atrial arrhythmia and is delivered within a ventricular refractory period to unpin one or more singularities associated with the atrial arrhythmia;

at least one second stage charge storage circuit selectively coupled to the at least one far field electrode that selectively stores a second stage of the three-stage atrial cardioversion therapy having at least five and less than ten far field pulses of less than 50% of a ventricular far-field excitation threshold with pulse coupling interval of between 70-100% of the cycle length of the atrial arrhythmia, wherein the second stage prevents repinning of the one or more singularities associated with the atrial arrhythmia that are unpinned by the first stage; and at least one third stage charge storage circuit selectively coupled to the near field electrode that selectively stores a third stage of the three-stage cardioversion therapy having at least five and less than ten near field pulses at a voltage of up to three times the atrial capture threshold with a pulse duration of more than 0.2 and less than 5 milliseconds and a pulse coupling interval of between 70-100% of the cycle length of the atrial arrhythmia, wherein the third stage extinguishes the one or more singularities associated with the atrial arrhythmia that are unpinned by the first stage and prevented from repinning by the second stage; and a battery system operably coupled and providing power to the sensing circuitry, the detection circuitry, the control circuitry and the therapy circuitry.

2. The apparatus of claim 1, wherein the first charge storage circuit includes at least one output capacitor configuration and a high voltage transformer electrically coupled to the battery system to charge the at least one output capacitor configuration.

3. The apparatus of claim 1, wherein the first charge storage circuit includes at least one output capacitor configuration and a charge pump electrically coupled to the battery system to charge the at least one output capacitor configuration.

4. The apparatus of claim 1, wherein the second charge storage circuit and third charge storage circuit include a single low voltage output capacitor configuration and switching circuitry between the single low voltage output capacitor configuration and the far field electrodes and the near field electrodes.

5. The apparatus of claim 1, wherein the control circuitry includes an H-bridge switching circuit operably connected to the electrodes to enable delivery of biphasic pulses.

6. The apparatus of claim 1, wherein the control circuitry controls delivery of the three-stage atrial cardioversion therapy to deliver in sequence one of the first stage, one of the second stage and one of the third stage.

7. The apparatus of claim 1, wherein the control circuitry controls delivery of the three-stage atrial cardioversion therapy to deliver in sequence one of the first stage, one of the second stage, one of the first stage, one of the second stage and one of the third stage.

8. The apparatus of claim 1, wherein the apparatus and the at least two leads include at least four far-field electrodes and the control circuitry is configured to selectively excite combinations of the far-field electrodes to create a plurality of different electric fields between different ones of the far-field electrodes to deliver a rotating set of electrical fields as a phased unpinning far-field therapy generated by the at least one first stage charge storage circuit and the at least one second stage charge storage circuit.

9. The apparatus of claim 1, wherein the control circuitry delivers each of the first stage, the second stage, and the third stage in accordance with a set of therapy parameters for the pulses of each stage that are programmed in response to feedback of a patient in whom the apparatus is implanted so as to provide an effective treatment of the atrial arrhythmia for the patient at a pain sensation that is tolerable to the patient.

10. The apparatus of claim 9, wherein the control circuitry comprises a microprocessor programmed with a heuristic learning algorithm that dynamically modifies settings of the set of therapy parameters for the pulses of each stage in response to an effectiveness of the three-stage atrial cardioversion therapy.

11. The apparatus of claim 1, wherein the pulse coupling interval of the first stage and the second stage is 88% of the atrial arrhythmia cycle length.

12. The apparatus of claim 1, wherein the first stage pulses are at least 10 volts and not more than 30 volts.

13. The apparatus of claim 1, wherein the first stage consists of two pulses.

14. The apparatus of claim 1, wherein the first stage has a total duration of 30% to 50% of one cycle length of the atrial arrhythmia.

15. The apparatus of claim 1, wherein each pulse of the first stage includes a total energy of 0.1 J or less.

16. The apparatus of claim 1, wherein the first stage pulses comprise biphasic pulses.

17. An atrial arrhythmia treatment apparatus, comprising:
an implantable therapy generator adapted to be implanted in a patient, including:
means for detecting an atrial arrhythmia and determining a cycle length of the atrial arrhythmia;
means for generating a three-stage atrial cardioversion therapy, including:
means for generating a first stage of the three-stage atrial cardioversion therapy having at least two and less than ten biphasic atrial cardioversion pulses of 10 volts to 100 volts for unpinning of one or more singularities associated with an atrial arrhythmia, wherein the first stage has a total duration of 30% to 50% of the cycle lengths of the atrial arrhythmia and is delivered within a ventricular refractory period;
means for generating a second stage of the three-stage atrial cardioversion therapy having at least five and less than ten far field pulses of less than a ventricular far-field excitation threshold with a pulse coupling interval of between 70-100% of the cycle length of the atrial arrhythmia for anti-repinning of the one or more singularities associated with the atrial arrhythmia; and
means for generating a third stage of the three-stage cardioversion therapy having at least five and less than ten near field pulses of one-and-a-half times to three-times the atrial capture threshold and a pulse coupling interval of between 70-100% of the cycle length of the atrial arrhythmia for extinguishing of the one or more singularities associated with the atrial arrhythmia; and
means for controlling delivery of the three-stage atrial cardioversion therapy in response to detection of the atrial arrhythmia with each stage having an inter-stage delay of between 50 to 400 milliseconds and without confirmation of conversion of the atrial arrhythmia until after delivery of the third stage; and at least two leads adapted to be operably connected to the implantable therapy generator, each lead having at least one electrode adapted to be positioned proximate an atrium of a heart of the patient through which the three-stage atrial cardioversion therapy is selectively delivered to the atrium of the heart, such that the means for generating the first stage and the means for generating the second stage are selectively coupled by the means for controlling delivery to a far-field configuration of the electrodes and the means for generating the third stage are selectively coupled by the means for controlling delivery to a near-field configuration of the electrodes.

18. The apparatus of claim 17, wherein the means for controlling delivery of the three-stage atrial cardioversion therapy delivers in sequence one of the first stage, one of the second stage and one of the third stage.

19. The apparatus of claim 17, wherein the means for controlling delivery of the three-stage atrial cardioversion therapy delivers in sequence one of the first stage, one of the second stage, one of the first stage, one of the second stage and one of the third stage.

20. The apparatus of claim 17, wherein the apparatus and the at least two leads include at least four far-field electrodes and the means for controlling delivery of the three-stage atrial cardioversion therapy is configured to selectively excite combinations of the far-field electrodes to create a plurality of different electric fields between different ones of the far-field electrodes to deliver a rotating set of electrical fields as a phased unpinning far-field therapy generated by the means for generating the first stage and the means for generating the second stage.

21. The apparatus of claim 17, wherein the means for controlling delivery of the three-stage atrial cardioversion therapy delivers each of the first stage, the second stage, and the third stage in accordance with a set of therapy parameters for the pulses of each stage that are programmed in response to feedback of a patient in whom the apparatus is implanted so as to provide an effective treatment of the atrial arrhythmia for the patient at a pain sensation that is tolerable to the patient 22. The apparatus of claim 21, wherein the means for controlling delivery further comprises a heuristic learning algorithm that dynamically modifies settings of the set of therapy parameters for the pulses of each stage in response to an effectiveness of the three-stage atrial cardioversion therapy.

23. The apparatus of claim 17, wherein the means for generating the three-stage atrial cardioversion therapy includes a battery system and the means for generating the first stage includes at least one output capacitor configuration and a high voltage transformer electrically coupled to the battery system to charge the at least one output capacitor configuration.

24. The apparatus of claim 17, wherein the means for generating the three-stage atrial cardioversion therapy includes a battery system and the means for generating the first stage includes at least one output capacitor configuration and a charge pump electrically coupled to the battery system to charge the at least one output capacitor configuration.

25. The apparatus of claim 24, wherein the means for generating the first stage includes a plurality of output capacitor configurations, one for each biphasic atrial cardioversion pulse, and the charge pump alternatively trickle charges each of the plurality of output capacitor configurations.

26. The apparatus of claim 17, wherein the at least two leads include a first lead having at least one far-field electrode and a second lead having at least one near-field electrode, and wherein the implantable pulse generator includes at least a portion of a housing of the implantable pulse generator that serves as a far-field electrode.

27. A method of treating atrial arrhythmias comprising:
(a) providing an atrial arrhythmia treatment device including an implantable therapy generator adapted to generate and selectively deliver a three-stage atrial cardioversion therapy and at least two leads operably connected to the implantable therapy generator, each lead having at least one electrode adapted to be positioned proximate the atrium of a heart of the patient;
(b) providing instructions for implanting the atrial arrhythmia treatment device in a patient during a surgical procedure;
(c) providing instructions for configuring the atrial arrhythmia treatment device at a time after completion of the surgical procedure, including instructions for programming the atrial arrhythmia treatment device with a set of therapy parameters for delivering a three-stage atrial cardioversion therapy to a patient via both a far-field configuration and a near-field configuration of the electrodes upon detection of an atrial arrhythmia by the atrial arrhythmia treatment device,
wherein the three-stage atrial cardioversion therapy includes:
a first stage of the three-stage atrial cardioversion therapy having at least two and less than ten atrial cardioversion pulses of at least 10 volts and not more than 100 volts for unpinning of one or more singularities associated with an atrial arrhythmia, the first stage having a total duration of less than two cycle lengths of the atrial arrhythmia and being delivered within a ventricular refractory period;
a second stage of the three-stage atrial cardioversion therapy having at least five and less than ten far field pulses of less than a ventricular far-field excitation threshold with a pulse duration of more than 5 and less than 20 milliseconds and a pulse coupling interval of between 70-100% of the cycle length of the atrial arrhythmia for anti-repinning of the one or more singularities associated with the atrial arrhythmia; and
a third stage of the three-stage cardioversion therapy having at least five and less than ten near field pulses at a voltage ranging from substantially one-and-a-half to three times the atrial capture threshold with a pulse duration of more than 0.2 and less than 5 milliseconds and a pulse coupling interval of between 70-100% of the cycle length of the atrial arrhythmia for extinguishing of the one or more singularities associated with the atrial arrhythmia, and
wherein the three-stage atrial cardioversion therapy is delivered in response to detection of the atrial arrhythmia with each stage having an inter-stage delay of between 50 to 400 milliseconds and without confirmation of conversion of the atrial arrhythmia until after delivery of the third stage.

\* \* \* \* \*